(12) United States Patent
Creissen

(10) Patent No.: US 10,408,805 B2
(45) Date of Patent: Sep. 10, 2019

(54) SYSTEM AND METHOD FOR SPRAY DEPOSITION OF A CHEMICAL ONTO A SUBSTRATE

(71) Applicant: HTX Technologies, LLC, Chapel Hill, NC (US)

(72) Inventor: Alain J. Creissen, Chapel Hill, NC (US)

(73) Assignee: HTX TECHNOLOGIES, LLC, Chapel Hill, NC (US)

( * ) Notice: Subject to any disclaimer, the term of this patent is extended or adjusted under 35 U.S.C. 154(b) by 0 days.

(21) Appl. No.: 15/900,754

(22) Filed: Feb. 20, 2018

(65) Prior Publication Data

US 2018/0238843 A1 Aug. 23, 2018

Related U.S. Application Data

(60) Provisional application No. 62/460,338, filed on Feb. 17, 2017.

(51) Int. Cl.
| | |
|---|---|
| *G01N 30/84* | (2006.01) |
| *B05D 1/02* | (2006.01) |
| *G01N 30/72* | (2006.01) |
| *G01N 1/40* | (2006.01) |
| *G01N 30/32* | (2006.01) |

(Continued)

(52) U.S. Cl.
CPC .......... *G01N 30/724* (2013.01); *B05B 1/005* (2013.01); *B05B 7/162* (2013.01); *B05D 1/02* (2013.01); *G01N 1/2813* (2013.01); *G01N 1/30* (2013.01); *G01N 1/312* (2013.01); *G01N 1/405* (2013.01); *G01N 30/32* (2013.01); *G01N 30/84* (2013.01);

(Continued)

(58) Field of Classification Search
CPC .......... B01J 37/0057; B01J 37/34; B01J 4/02; B01L 3/0268; G01N 2035/1041; H01J 49/0404; H01J 49/0445; H01J 49/0477
USPC ...................... 250/282, 288, 281, 423 R, 425
See application file for complete search history.

(56) References Cited

U.S. PATENT DOCUMENTS

| | | | |
|---|---|---|---|
| 5,772,964 A | 6/1998 | Prevost et al. | |
| 7,335,897 B2 * | 2/2008 | Takats | H01J 49/0404 250/282 |

(Continued)

FOREIGN PATENT DOCUMENTS

CN 204107742 U 1/2015

OTHER PUBLICATIONS

EPO, Extended European Search Report for European Patent Application No. 18000156, dated Jul. 10, 2018.

*Primary Examiner* — David A Vanore
(74) *Attorney, Agent, or Firm* — NK Patent Law

(57) ABSTRACT

The presently disclosed subject matter is directed to a system for depositing a chemical of one or more components onto a medium. The system includes a spray assembly for depositing the chemical, a medium for collecting the one or more components forming the chemical, and an enclosure for housing the medium and the spray assembly. The spray assembly includes a capillary for receiving and ejecting a fluid containing the one or more components, a nozzle for receiving and ejecting a gas towards both the medium and the fluid when the fluid is ejected from the capillary, and a spray heater for heating the capillary and the gas. The enclosure includes a translatable drawer for supporting and translating the medium. The system further includes a medium heater for heating the medium.

21 Claims, 36 Drawing Sheets

(51) Int. Cl.
  *B05B 1/00* (2006.01)
  *B05B 7/16* (2006.01)
  *G01N 1/28* (2006.01)
  *G01N 1/30* (2006.01)
  *G01N 1/31* (2006.01)
  *G01N 1/02* (2006.01)

(52) U.S. Cl.
  CPC . *G01N 2001/028* (2013.01); *G01N 2030/324* (2013.01)

(56) References Cited

U.S. PATENT DOCUMENTS

| | | | |
|---|---|---|---|
| 8,287,938 B1 * | 10/2012 | Scheer | B05D 1/12 239/9 |
| 2003/0228240 A1 | 12/2003 | Dwyer | |
| 2009/0202731 A1 | 8/2009 | Kazkaz et al. | |
| 2016/0121323 A1 | 5/2016 | Greef et al. | |

* cited by examiner

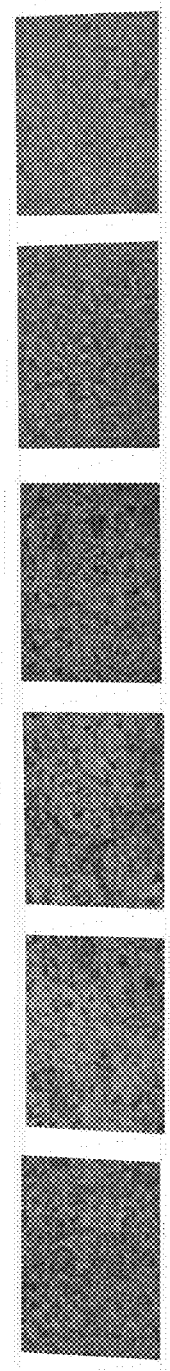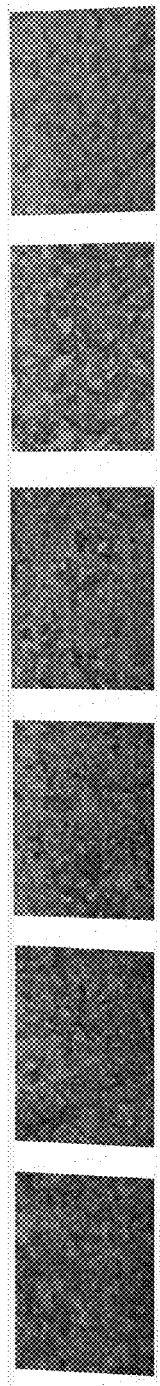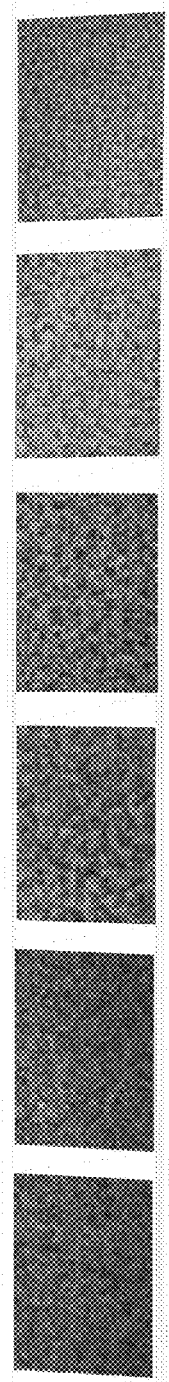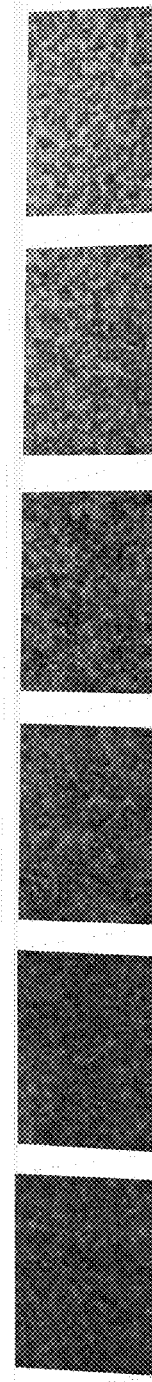

m/z 806.3 +/- 0.5Da m/z 885.3 +/- 0.5Da m/z 888.4 +/- 0.5Da m/z 906 Da +/- 0.5Da

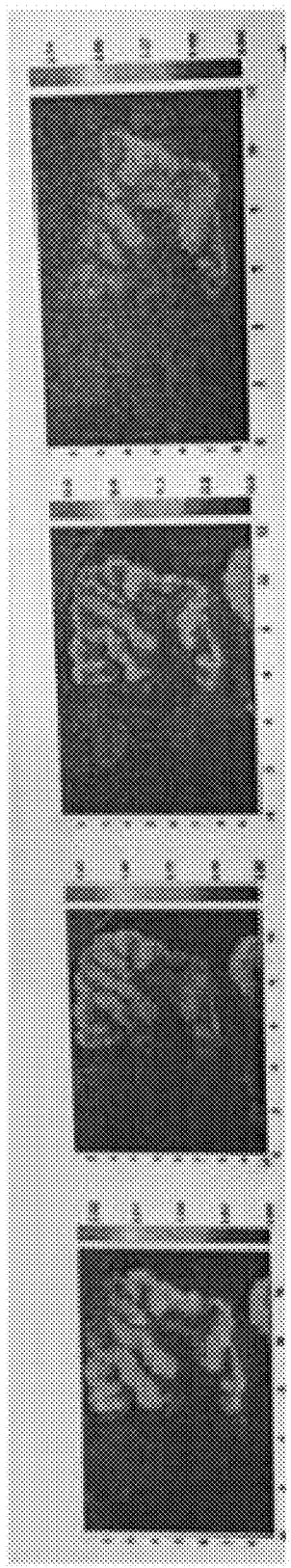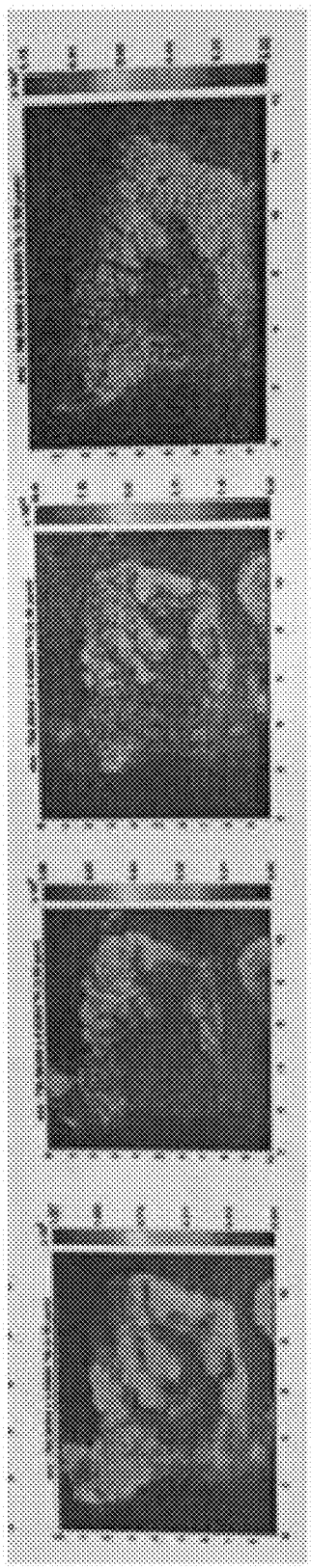

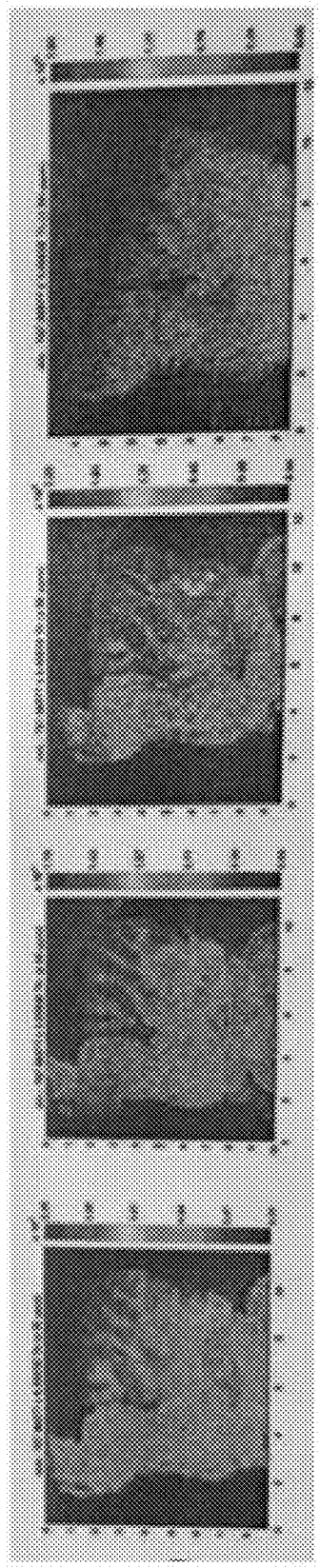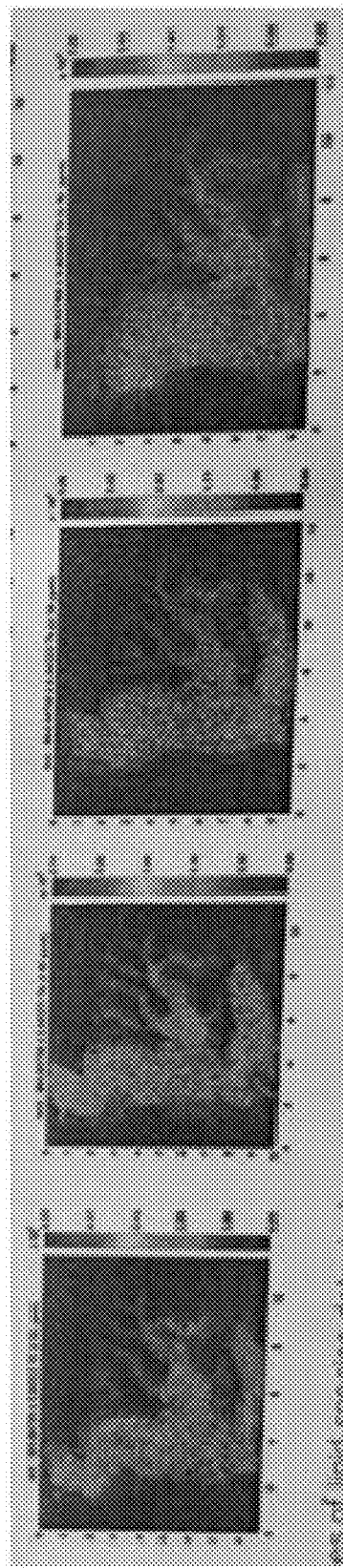
FIG. 16a  FIG. 16b  FIG. 16c  FIG. 16d
FIG. 17a  FIG. 17b  FIG. 17c  FIG. 17d

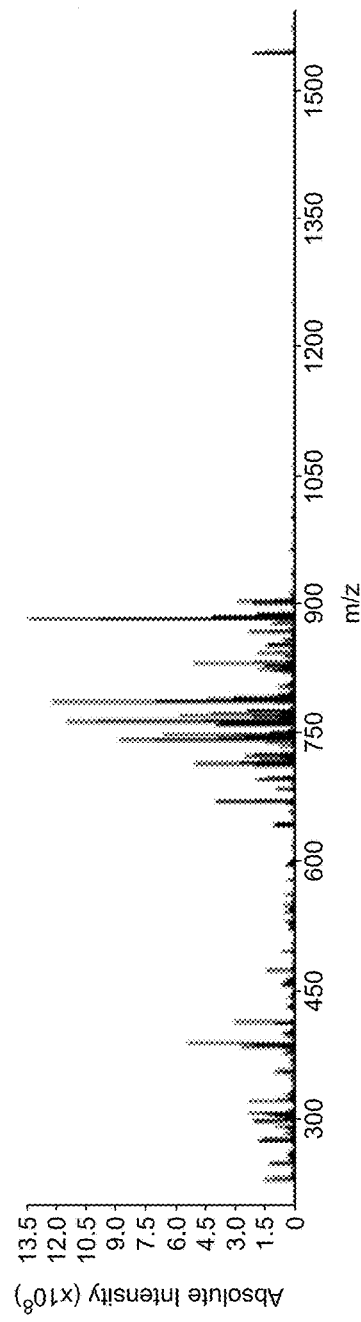
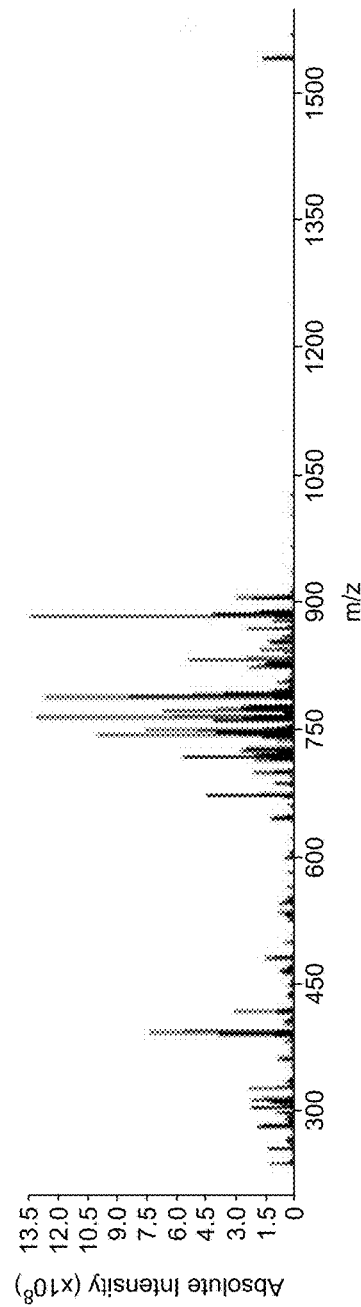
FIG. 24a
FIG. 24b

SYSTEM AND METHOD FOR SPRAY DEPOSITION OF A CHEMICAL ONTO A SUBSTRATE

CROSS-REFERENCE TO RELATED APPLICATIONS

This application claims priority to and the benefit of U.S. Provisional Patent Application No. 62/460,338, filed Feb. 17, 2017, which is incorporated by reference herein in its entirety.

TECHNICAL FIELD

The presently disclosed subject matter is generally directed to systems and methods for spray deposition of one or more chemicals onto a substrate. Specifically, embodiments of the present disclosure relate to a system and method for spray deposition of dissolved reactive and non-reactive chemicals onto biological sample surfaces for subsequent analysis by mass spectrometry.

BACKGROUND

Systems and methods for spray deposition of chemicals prior to analysis are well known. However, while various spray assemblies have been developed for coating a planar surface, the desire for enhanced quantitative and qualitative controls of chemical deposition continues to exist. Particularly, analysis techniques improve the location, size, penetration, and physical parameters affecting the deposition step. In addition, the drying and incubation of the dissolved chemicals onto the tissue surface greatly affects the signal intensity and the spatial resolution attainable on the analyzer. Further, the chemical nature of the chemical deposition and the chemical reactions within the tissue are affected by the spraying gas, chamber, concentration of the chemicals in solution, and the composition of the solvent mixture, as reflected in the analytical results. Further, as analysis techniques continue to diversify, the ability to customize each chemical spray deposition for new analysis processes can be useful. Accordingly, it would be beneficial to provide a chemical deposition system and method that enables enhancement of the uniformity of chemical deposits, greater control over solvent evaporation, and more efficient and error-free operation.

SUMMARY

In some embodiments, the presently disclosed subject matter is directed to a system for depositing a chemical layer of one or more components onto a medium. The system comprises a spray assembly for depositing the chemical layer. The spray assembly includes a capillary for receiving and ejecting a fluid (e.g., a liquid chemical) comprising the one or more components, wherein the capillary comprises an exit (e.g., a tip) through which the fluid is sprayed; a nozzle body configured to channel a gas towards the exit of the capillary and configured to atomize a fluid into a directional spray that delivers droplets with a diameter of 0.1-1.0 microns onto a medium; and a heat exchanger housed in the nozzle body for heating the capillary and the gas. The system further includes an enclosure for housing the medium and the spray assembly, wherein the enclosure comprises a translatable drawer for supporting and translating the medium and a fan venting system for exhausting solvent fumes.

In some embodiments, the spray assembly is translatable in two directions (e.g., perpendicular directions) for maneuvering the spray assembly with respect to the medium at a nozzle velocity of about 1,200 to 5,600 mm/min.

In some embodiments, the translatable drawer comprises a medium heater and/or medium cooler configured to heat and/or cool the medium to temperatures of about −20° C. to 120° C.

In some embodiments, the system further comprises an atmosphere conditioning system configured to regulate humidity, pressure, temperature, or combinations thereof of air above the medium. In some embodiments, the air above the medium is regulated during use, such as before or during a spraying step, an incubation step, or both.

In some embodiments, the enclosure comprises a front viewing panel positioned above a front panel of the translatable drawer. In some embodiments, the enclosure comprises a gutter positioned within the enclosure interior on at least one panels for collecting fluid so that waste materials are contained when the translatable drawer is open.

In some embodiments, the drawer comprises a medium support tray that includes inserts, position measurements, pre-defined positions for laboratory equipment, or combinations thereof. In some embodiments, the drawer provides no viewing bias such that the operator is able to freely view the sample medium before, during and/or after spraying.

In some embodiments, the spray assembly is configured to adjust the fluid flow rate in relation to the nozzle velocity to a linear flow rate of less than about 0.00001 ml/mm (e.g., super dry conditions).

In some embodiments, the spray assembly is configured to calculate a spray humidity measurement to allow maximizing of nozzle velocity and fluid flow rate for super fast spray deposition (e.g., 18,000 mm/min or less), wherein the spray humidity measurement is selected from calculated linear flow rate, sensor-controlled evaporation rate, or combinations thereof.

In some embodiments, the spray assembly is configured to spray in a defined spray pattern, wherein the spray pattern is selected from Swiss Cross, automatic square, non-overlapping, diagonal, and combinations thereof.

In some embodiments, the system is configured to decrease the matrix crystal size below 10 micron, enable the use of difficult-to-dry matrices, and/or allow the use of environmentally friendly solvent mixtures comprising a greater weight percent of water, methanol, or both compared to a relatively smaller weight percent of highly volatile solvents.

In some embodiments, the system includes a humidity chamber to perform one or more temperature and humidity-controlled reactions, selected from enzymatic digestion, derivatization, rehydration, or combinations thereof.

In some embodiments, the drawer includes a motorized open and close feature and/or a gripping feature, such as to allow manual drawer translation or integration with a robotic device.

In some embodiments, the spray heater includes a fluid spray heater, a gas spray heater, or both. In some embodiments, both the fluid spray heater and the gas spray heater are each independently operable and capable of being set at different temperatures, relative to the other.

In some embodiments, the system includes an external heater and/or cooler for heating and/or cooling fluid, gas, or both before being received by the spray assembly.

In some embodiments, the system includes one or more additional capillaries, wherein each capillary is configured for receiving and ejecting one or more additional fluids. In some embodiments, the fluids comprise one or more secondary components.

In some embodiments, the system includes one or more additional nozzles, wherein each nozzle is configured for receiving and ejecting one or more gases towards the medium, the fluid, or both when the fluid is ejected from the capillary.

In some embodiments, the system includes one or more switching valves for switching from a first fluid or gas to a second fluid or second gas, wherein each switching valve optionally comprises a combination of a selector valve and multiple loop valves capable of maintaining a constant flow rate while changing fluid or gas type.

In some embodiments, the system includes a software-controlled solvent pump, a selector valve, and/or one or more switching valves to allow automated start-up, medium spraying, cleaning sequence, and/or shut-down.

In some embodiments, the system includes a fluid line and capillary capable of withstanding solvent pressure greater than 14.7 psi, and/or optional fluid degassing capability capable of bringing a fluid within the fluid line or capillary to its boiling point temperature at ambient pressure.

In some embodiments, the nozzle body and heat exchanger are configured with a height, width, or both of less than about 3.5 inches.

In some embodiments, the presently disclosed subject matter is directed to a method of depositing a chemical layer of one or more components onto a medium using the disclosed system. Particularly, the system comprises a spray assembly for depositing the chemical layer. The spray assembly includes a capillary for receiving and ejecting a fluid comprising the one or more components, wherein the capillary comprises a exit through which the fluid is sprayed; a nozzle body configured to channel a gas towards the exit of the capillary and configured to atomize a fluid into a directional spray that delivers droplets with a diameter of 0.1-1.0 microns onto a medium; and a heat exchanger housed in the nozzle body for heating the capillary and the gas. The system further includes an enclosure for housing the medium and the spray assembly, wherein the enclosure comprises a translatable drawer for supporting and translating the medium and a fan venting system for exhausting solvent fumes. The method comprises translating the drawer to an open position, wherein the drawer comprises a support, positioning the medium on the support, translating the drawer to a closed position (where the medium is positioned adjacent to the spray assembly and within an interior compartment of the spray deposition system when the drawer is closed), and atomizing a stream of chemical from the nozzle onto the medium.

In some embodiments, the presently disclosed subject matter is directed to a method of calibrating a chemical deposition sprayer using the disclosed spray deposition system. The system comprises a spray assembly for depositing the chemical layer. The spray assembly includes a capillary for receiving and ejecting a fluid comprising the one or more components, wherein the capillary comprises an exit through which the fluid is sprayed; a nozzle body configured to channel a gas towards the exit of the capillary and configured to atomize a fluid into a directional spray that delivers droplets with a diameter of 0.1-1.0 microns onto a medium; and a heat exchanger housed in the nozzle body for heating the capillary and the gas. The system further includes an enclosure for housing the medium and the spray assembly, wherein the enclosure comprises a translatable drawer for supporting and translating the medium and a fan venting system for exhausting solvent fumes. The method comprises selecting a preset method with a set dryness level, and spraying a chemical layer onto a reference medium, calibration plate, and/or sensor to measure dryness level of the chemical layer sprayed. The dryness level is then compared to a set (reference) level. In some embodiments, one or more spray parameters can be adjusted to achieve a set dryness level (e.g., enclosure temperature, humidity level, heated tray temperature, nozzle temperature, and/or gas flow rate of the disclosed chemical deposition system). In some embodiments, a validation spray can be performed to confirm that the adjustment is adequate. After calibration, a medium is deposited in the enclosure as set forth above, and a chemical layer of one or more components can then be deposited on the medium via a spray nozzle.

In some embodiments, the presently disclosed subject matter is directed to a method of spraying a chemical layer of one or more components onto a medium using the disclosed spray deposition system. The system comprises a spray assembly for depositing the chemical layer. The spray assembly includes a capillary for receiving and ejecting a fluid comprising the one or more components, wherein the capillary comprises an exit through which the fluid is sprayed; a nozzle body configured to channel a gas towards the exit of the capillary and configured to atomize a fluid into a directional spray that delivers droplets with a diameter of 0.1-1.0 microns onto a medium; and a heat exchanger housed in the nozzle body for heating the capillary and the gas. The system further includes an enclosure for housing the medium and the spray assembly, wherein the enclosure comprises a translatable drawer for supporting and translating the medium and a fan venting system for exhausting solvent fumes. In some embodiments, the system comprises a multiple-port valve (e.g., 8 port valve with 2 loops) to load a first solution into a loop, while a push solvent travels through the nozzle. The nozzle then is raised or lowered to a desired temperature and stable spray conditions are maintained. A medium is positioned below the spray nozzle, and the valve is switched such that spray deposition of the first solution is initiated. The medium is maintained within the interior enclosure of the disclosed system. Alternatively, the medium can be positioned within a heated and/or humid chamber (e.g., a humidity chamber) where one or more specific reactions (e.g., enzymatic digestion) occur. After a set period of time, the medium is brought back inside the interior compartment of the system enclosure and a second solution is loaded into a loop and a push solvent is sprayed through the nozzle. Spray deposition of the second solution is then performed. In some embodiments, an optional cleaning sequence can be run before the system is shut down or before the system moves to a new sample or method.

BRIEF DESCRIPTION OF THE DRAWINGS

The previous summary and the following detailed descriptions are to be read in view of the drawings, which illustrate particular exemplary embodiments and features as briefly described below. The summary and detailed descriptions, however, are not limited to only those embodiments and features explicitly illustrated.

FIG. 2b is a perspective view of the sprayer of FIG. 2a.

FIG. 3b is a side plan view of the chemical deposition sprayer of FIG. 3a.

FIGS. 9a-10f are magnified photographs of matrix-coated slides of on-tissue sample areas.

FIGS. 11a-12f are magnified photographs of matrix-coated slides of off-tissue sample areas.

FIGS. 14a-14d are MS images of lipid species detected on 4 samples of rat brain with m/z value of 756.55138, PC (16:0/16:0)+Na.

FIGS. 15a-15d are MS images of lipid species detected on 4 samples of rat brain with m/z value of 760.58508, PC (16:0/18:1)+H.

FIGS. 16a-16d are MS images of lipid species detected on 4 samples rat brain with m/z value of 767.56977, phSM (16:0/22:5)+H.

FIGS. 17a-17d are MS images of lipid species detected on 4 samples of rat brain with m/z value of 864.64768.

FIG. 24a is a graph of absolute intensity versus m/z illustrating the comparison of overall spectra at 1300 mm/min.

FIG. 24b is a graph of absolute intensity versus m/z illustrating the comparison of overall spectra at 2600 mm/min.

DETAILED DESCRIPTION

The presently disclosed subject matter is introduced with sufficient details to provide an understanding of one or more particular embodiments of broader inventive subject matters. The descriptions expound upon and exemplify features of those embodiments without limiting the inventive subject matters to the explicitly described embodiments and features. Considerations in view of these descriptions will likely give rise to additional and similar embodiments and features without departing from the scope of the presently disclosed subject matter.

Unless defined otherwise, all technical and scientific terms used herein have the same meaning as commonly understood to one of ordinary skill in the art to which the presently disclosed subject matter pertains. Although any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in the subject specification, including the claims. Thus, for example, reference to "a sprayer" can include a plurality of such sprayers, and so forth.

Unless otherwise indicated, all numbers expressing quantities of components, conditions, and so forth used in the specification and claims are to be understood as being modified in all instances by the term "about". Accordingly, unless indicated to the contrary, the numerical parameters set forth in the instant specification and attached claims are approximations that can vary depending upon the desired properties sought to be obtained by the presently disclosed subject matter.

As used herein, the term "about", when referring to a value or to an amount of mass, weight, time, volume, concentration, and/or percentage can encompass variations of, in some embodiments +/−20%, in some embodiments +/−10%, in some embodiments +/−5%, in some embodiments +/−1%, in some embodiments +/−0.5%, and in some embodiments +/−0.1%, from the specified amount, as such variations are appropriate in the disclosed packages and methods.

Figure 1:
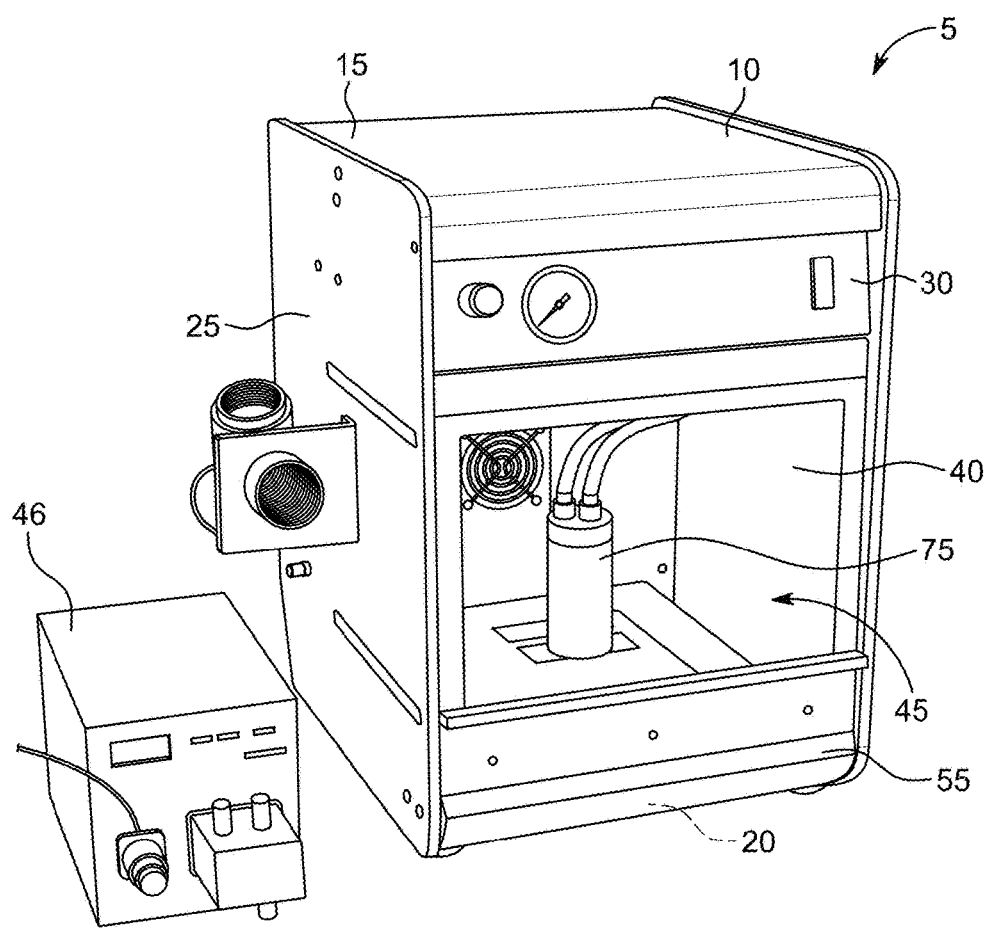
FIG. 1 is a perspective view of a chemical deposition system in accordance with some embodiments of the presently disclosed subject matter.

The presently disclosed subject matter is directed to a spray deposition system that can be used to achieve reliable, consistent chemical deposition onto a substrate. The term "spray deposition" as used herein refers to a process in which dissolved materials are sprayed onto a surface. As illustrated in FIG. 1, system 5 includes sprayer 10 comprising spray assembly 75 that provides a stream of material to be deposited on a sample medium. The system further includes top panel 15, bottom panel 20, side panels 25, front panel 30, and rear panel 35. As shown, front panel 30 can include viewing panel 40. As set forth in more detail herein below, the disclosed sprayer further includes sample drawer 55 that opens and closes as needed to allow a user to position a sample medium within sprayer interior compartment 45. One embodiment of an eluent delivery pump is illustrated at 46.

Figure 2A:
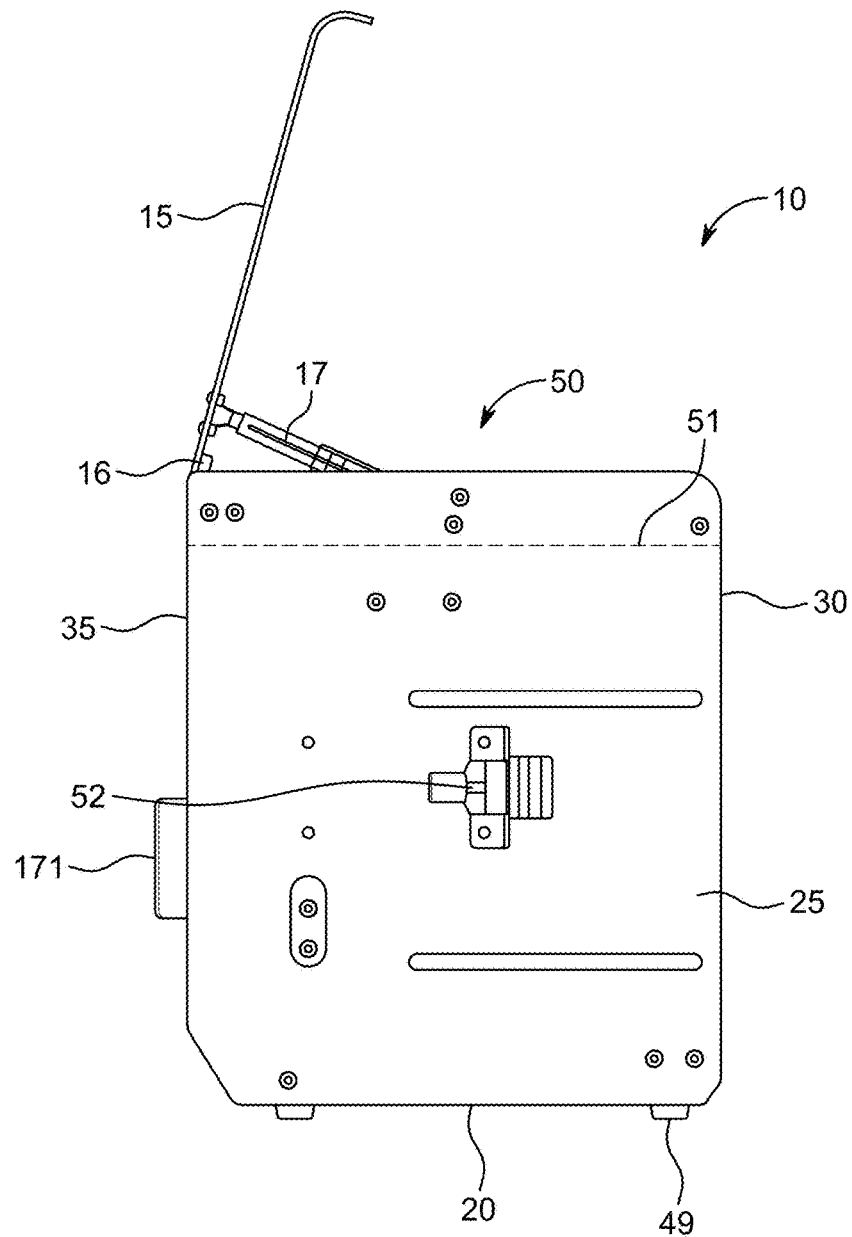
FIG. 2a is a side plan view of a chemical deposition sprayer in accordance with some embodiments of the presently disclosed subject matter.
Figure 2B:
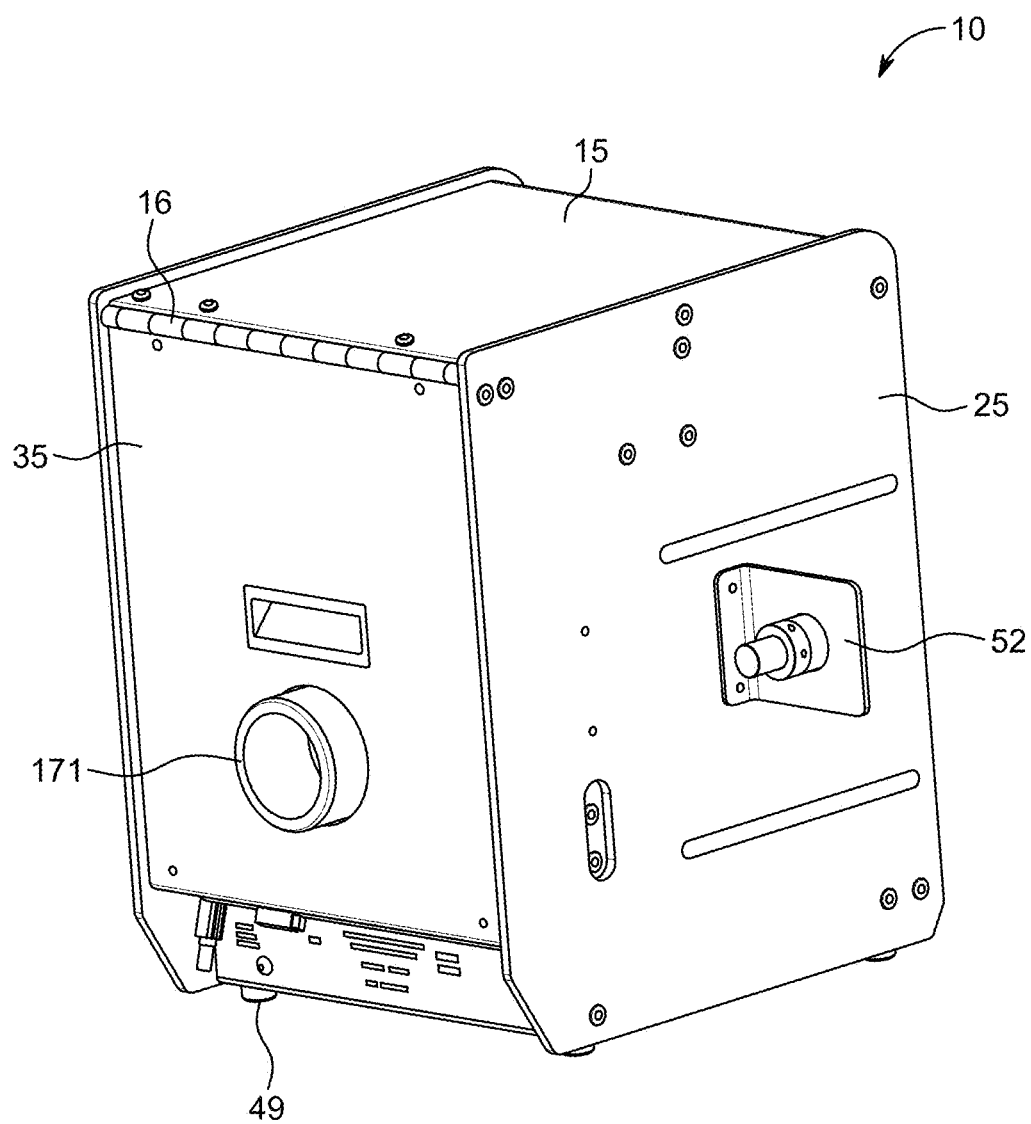

As illustrated in FIGS. 2a and 2b, in some embodiments, top panel 15 of sprayer 10 can be raised and lowered to allow a user to access upper compartment 50, positioned between the top panel and compartment panel 51 positioned in sprayer interior compartment 45. To this end, top panel 15 can include a mechanism (such as hinge 16) to allow movement of the panel between an open and closed position. In some embodiments, the upper panel can be configured with one or more supports 17 to maintain the top panel in the open configuration for a desired period of time. The supports can fold away or be removed when the top panel is in the closed position. Alternatively, in some embodiments, top panel 15 can be removable so that in use a user can completely remove the top panel to gain access to the upper compartment. Upper compartment 50 can house a wide variety of components, including (but not limited to) switches, sensors, electronics, wiring, tubing, displays, and/or other operating components. The top panel thus can protect the components from exposure to the outside environment. In addition, top panel 15 allows a user to access the internal components of the device for repairs, trouble shooting, maintenance, and the like. In use, access can be provided to the components by removing and/or pivoting top panel 15 and placing upper compartment 50 in an accessible position without exposing interior compartment 45 to the external environment.

As shown in FIGS. 2a and 2b, in some embodiments, sprayer 10 can include a plurality of feet 49 to provide stability to the device. In some embodiments, feet 49 can be adjustable, such as to level the sprayer when placed on an uneven surface. The feet can also be used to the raise the height of sprayer 10 to a desired level. Further, the feet add stability to the sprayer, such as to minimize vibrations and the like. It should be appreciated that feet 49 are optional and the presently disclosed subject matter includes sprayer embodiments that lack feet.

FIG. 2b illustrates that sprayer 10 can further include selector valve 52 that selects between two or more positions that alter the flow path of a fluid. For example, the selector valve can be used to alternate the source fluid between a fluid used during spray deposition to a fluid used for conditioning and/or washing applications. The selector valve can be manually adjusted by a user, or it can be automatically updated using a computer or other control mechanism.

Figure 3A:
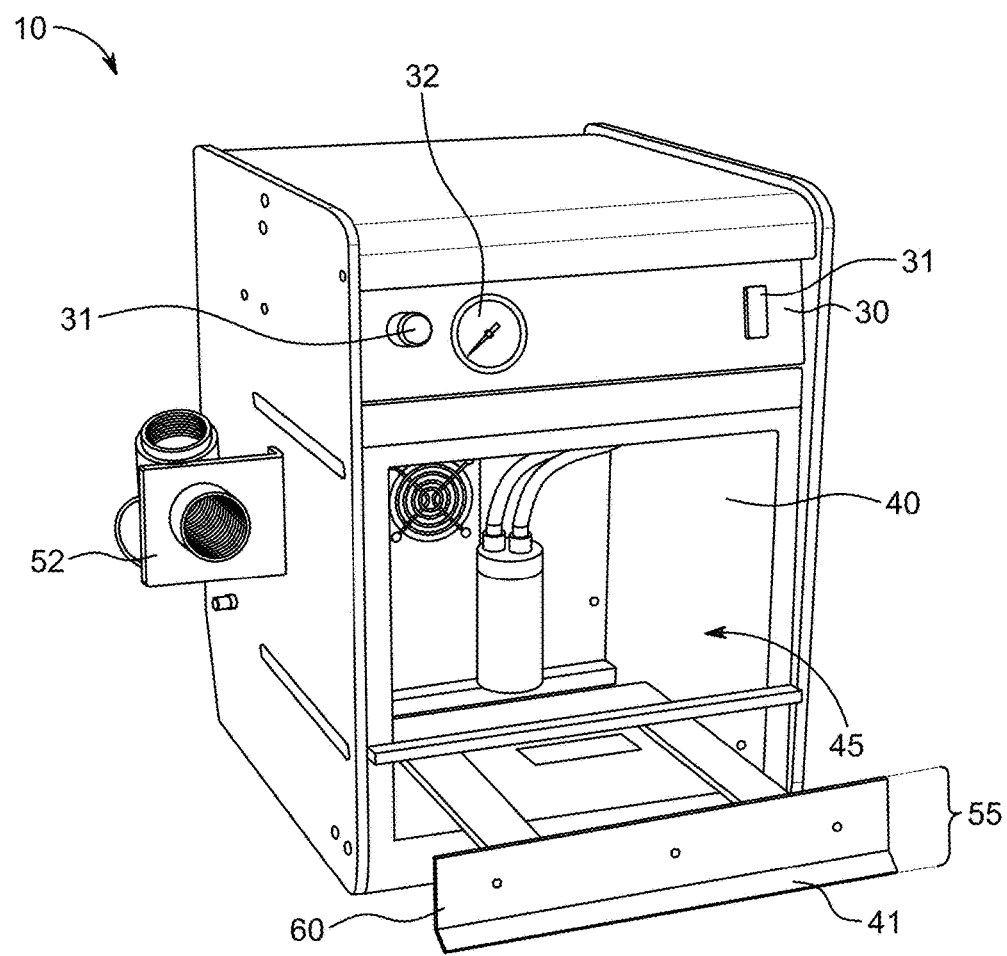
FIG. 3a is a perspective view of a chemical deposition sprayer comprising a drawer in accordance with some embodiments of the presently disclosed subject matter.

As shown in FIG. 3a, front panel 30 of the disclosed sprayer comprises viewing panel 40. Viewing panel 40 can be at least partially transparent to allow a user to view sprayer interior compartment 45. To this end, the viewing panel can be constructed from any known transparent or partially transparent material, such as (but not limited to) glass, plexiglass, plastic, and the like. In some embodiments, the viewing pane can be tinted, polarized, UV-protected, and the like as desired by a user. In some embodiments, internal compartment 45 can include one or more light sources to illuminate the contents of the internal compartment for viewing. Suitable light sources can include (but are not limited to) fluorescent bulbs, incandescent lights, LEDs, and the like. The light source can be switched on and off manually or through an automatic control (e.g., when the sprayer is activated). Interior compartment 45 of the disclosed sprayer can be accessed when desired. For example, front viewing panel 40 can be selectively fastened to the sprayer and/or to other panels for permitting access to the interior compartment and/or to components housed within the interior compartment (e.g., gutter, axis, spray assembly, sections, connections, filters, sensors, and/or any other portion of the system, as described in more detail herein below). It should be appreciated that any desired panel can be configured to be removable, not just viewing panel 40 (e.g., front panel, top panel, bottom panel, back panel, and/or side panels).

In some embodiments, front panel 30 comprises one or more controls 31 and/or displays 32 that can be used to manage sprayer 10. For example, controls 31 and displays 32 can include a power switch, temperature display, pressure display, safety valve, and the like. It should be appreciated that the controls/displays can be configured on one or more panel, and are not limited to front panel 30.

Figure 3B:
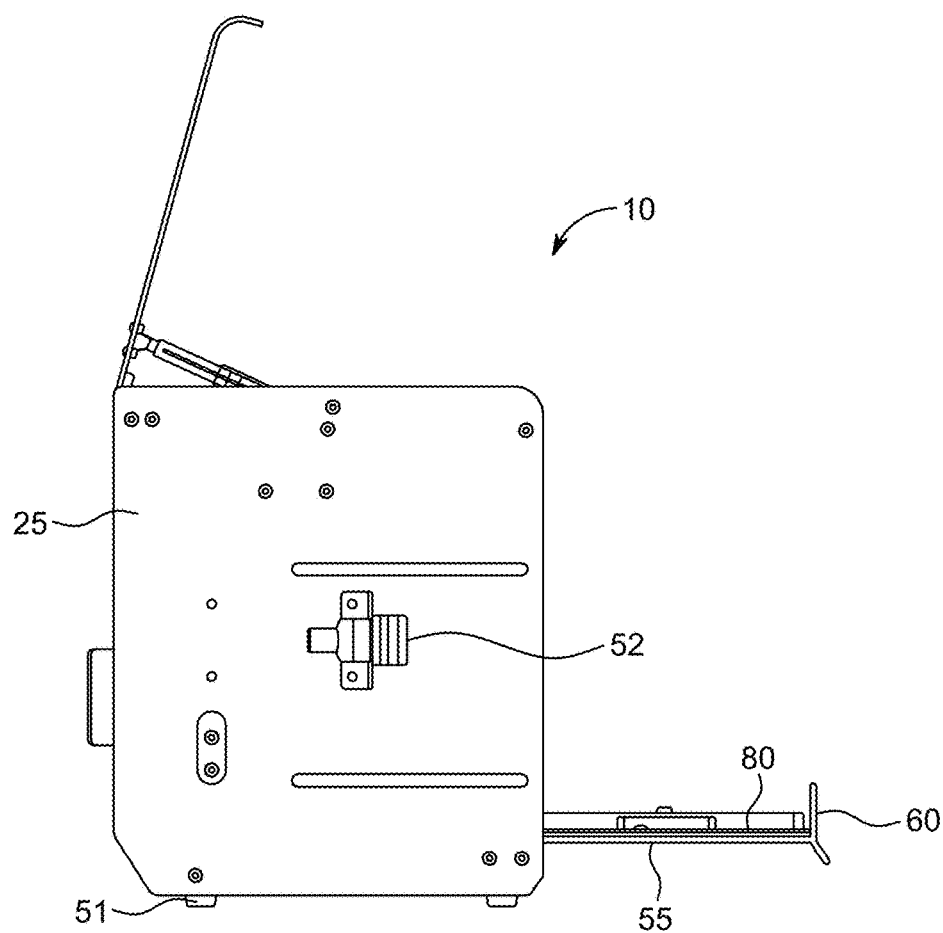

Front panel 30 includes movable drawer 55 that can be used for supporting and translating a sample medium to and from interior compartment 45. As shown in FIG. 3a, drawer 55 can include front panel 60 positioned proximal to and below front viewing panel 40. In some embodiments, the front panel includes one or more gripping features 41 (such as a handle, textured area, and/or protuberance) to assist the user when opening and closing the drawer manually. The presently disclosed subject matter also includes embodiments wherein the drawer can open and close mechanically (e.g., pushing a button, programming a computer, etc.). When front panel 60 of drawer 55 is translated away from interior compartment 45, the sprayer is configured in an open position, exposing the interior compartment to the external environment, as depicted in FIGS. 3a and 3b. Advantageously, exposure of interior compartment 45 to the external environment is minimized because viewing panel 40 remains in a static position when the drawer is translated. When the drawer is in the closed position, the interior compartment is sealed and/or isolated from the external environment by the front, top, bottom, rear, and side panels.

Drawer 55 can be translated from the open to closed position using any mechanism known or used in the art. For example, the drawer can be configured to move along one or more tracks affixed to the bottom of the interior compartment. However, the presently disclosed subject matter is not limited and the drawer can move using any known mechanism, such as through one or more mechanical arms.

Figure 3C:
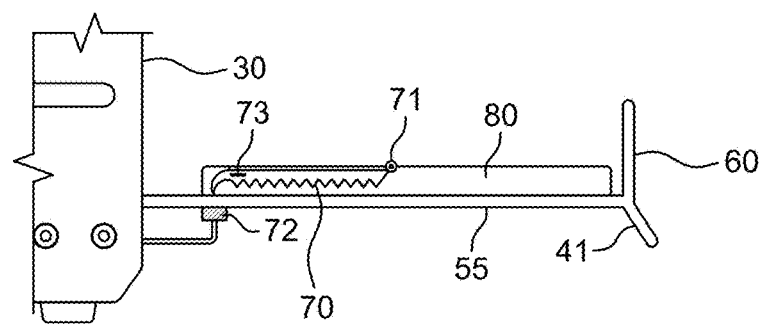
FIG. 3c is a side plan view of a sprayer drawer in accordance with some embodiments of the presently disclosed subject matter.

As shown in FIG. 3c, drawer 55 includes base 80 for supporting a medium. In some embodiments, base 80 can be a tray or can support a tray. The medium can include any suitable sample medium, including (but not limited to) microscope glass slides, metal plates, and/or plastic plates. Base 80 can be constructed from any rigid material known or used in the art, capable of supporting the weight of the medium. For example, in some embodiments, the base can be constructed from one or more rigid polymeric materials, metals (e.g., stainless steel and the like), or combinations thereof. Drawer 55 can further include one or more heating/cooling elements 70 that can be used to raise or lower the temperature of the sample medium. The heating/cooling elements function to maintain the medium at a predetermined temperature. Heating/cooling element 70 can be powered using any mechanism, such as (but not limited to) the use of power cable 72. The drawer can further include one or more temperature sensors 73 (such as a thermistor, RTD, and/or thermocouple) to ensure a desired temperature is maintained. In some embodiments, conductive plate 71 can be positioned on base 80, between the heating/cooling element and a sample medium, as shown in FIG. 3c. Plate 71 can be constructed from any conductive material, such as (but not limited to) stainless steel, copper, aluminium, iron, or any other metal. In some embodiments, the conductive plate is constructed from a material with low thermal capacity, so that the temperature of the plate can quickly change in the course of heating, with less power consumption and prompt control on temperature variance.

Figure 4A:
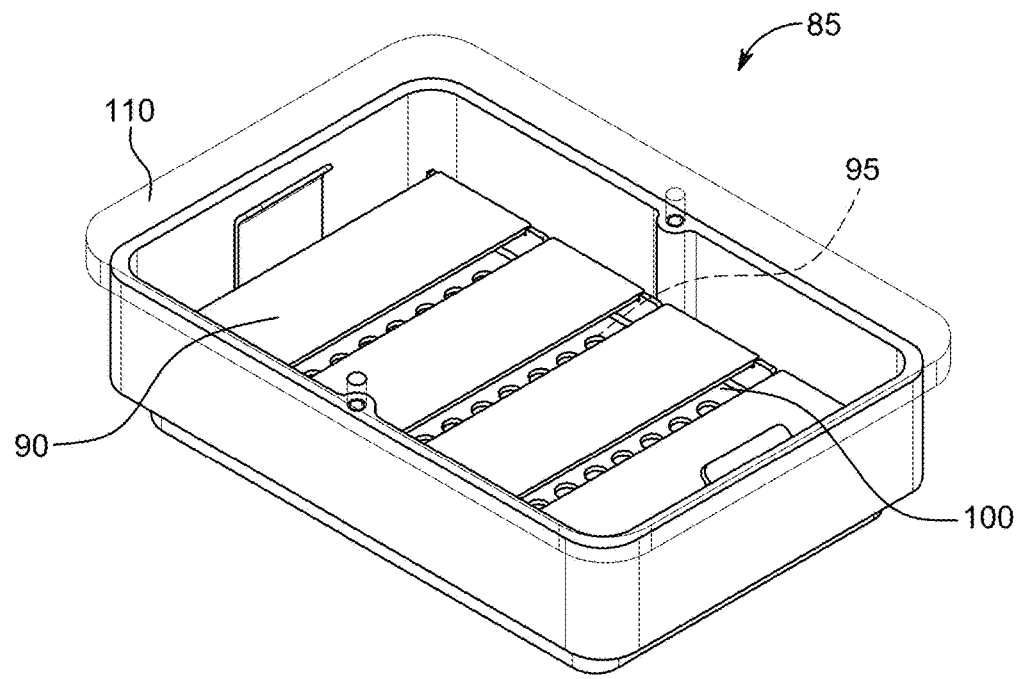
FIG. 4a is a perspective view of a humidity chamber in accordance with some embodiments of the presently disclosed subject matter.
Figure 4B:
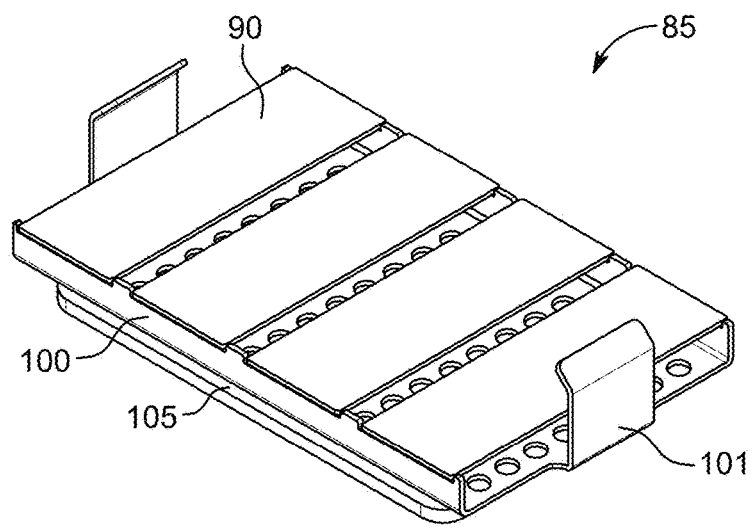
FIG. 4b is a perspective view of a humidity chamber in accordance with some embodiments of the presently disclosed subject matter.
Figure 4C:
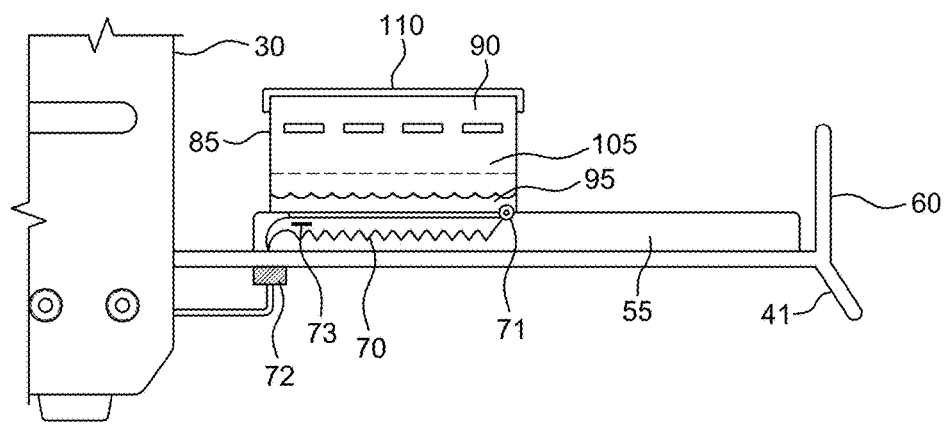
FIG. 4c is a side plan view of a humidity chamber positioned on the drawer of a sprayer in accordance with some embodiments of the presently disclosed subject matter.

In some embodiments, the sample medium can be configured in humidity chamber 85. For example, the humidity chamber can be positioned on drawer 55 (e.g., base 80, a tray, or plate 71) to create a desired chemical reaction condition (e.g., enzymatic digestion at 37° C.). FIGS. 4a-4c illustrate one embodiment of humidity chamber 85, configured with sample medium 90 (e.g., 4 microscope slides) positioned above liquid 95. As shown, the humidity chamber can include one or more adaptors 100 that are sized and shaped to house at least one sample medium. In some embodiments, the adaptor is removable and can be replaced with a different adaptor sized and shaped to house a different sample medium (e.g., larger or smaller glass slides). The adaptor can include one or more handles 101 to allow for easy removal and/or positioning within the humidity chamber. In some embodiments, the adaptor can rest on grid 105 to ensure the sample medium does not directly contact liquid 95 positioned within the bottom of the chamber, as shown in FIG. 4c. In some embodiments, the grid can include one or more apertures to allow water and/or air to pass therethrough.

Alternatively, the humidity chamber can be configured without adaptor 100, and the sample mediums can rest directly on grid 105. The grid, adaptor, and sample medium are positioned above liquid 95. Liquid 95 can include any suitable liquid, including (but not limited to) water, buffer, and the like. Adaptor 100 and/or grid 105 thus ensure that the sample medium is stable and protected during movement, such as when the drawer opens and closes. The humidity chamber can include cover 110 that removably fits over the top (open) surface of the humidity chamber. In some embodiments, the interior of the humidity chamber can include a sensor to detect humidity level, temperature, etc.

In use, after the sample medium is positioned on drawer 55, the drawer is translated to the closed position, where the sample medium is positioned within interior compartment 45 for spray deposition. Interior compartment 45 comprises spray assembly 75 that enables the spray deposition of a chemical layer of one or more components onto medium 90. Particularly, the spray assembly houses a chemical solution that is sprayed on a substrate medium and is evaporated upon deposition. In some embodiments, the chemical solution can include one or more internal standards, derivatization agents, enzymes (e.g., trypsin), matrices (e.g., MALDI matrices), extracting solvents (e.g., chloroform), and/or rehydrating solvents (e.g., as water, ammonium bicarbonate). Advantageously, interior compartment 45 can be sealed and/or isolated from the external environment by the front, top, bottom, back, and side panels.

Figure 4D:
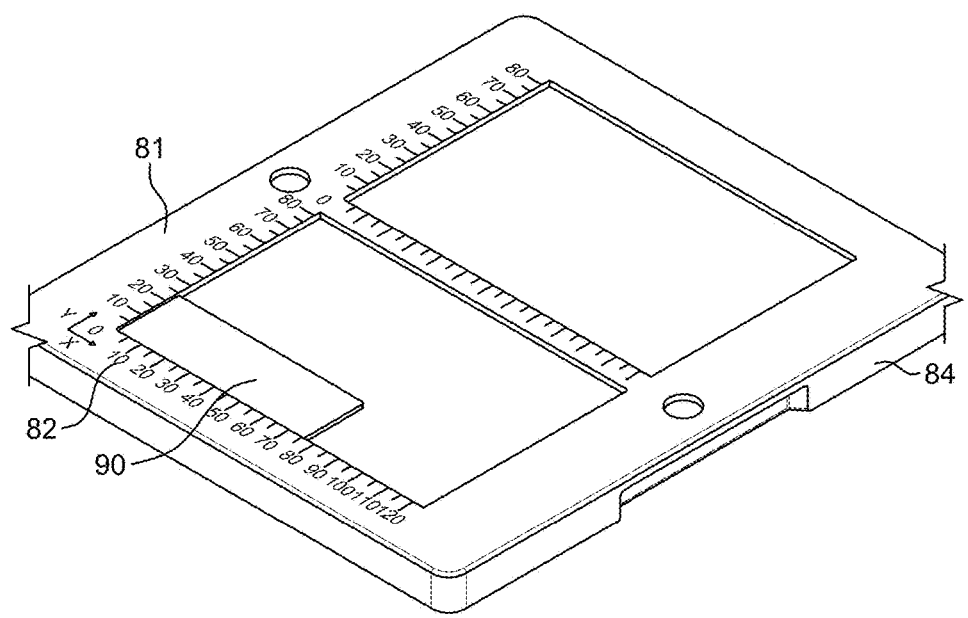
FIG. 4d is one embodiment a tray that can rest on a drawer base in accordance with some embodiments of the presently disclosed subject matter.
Figure 4E:
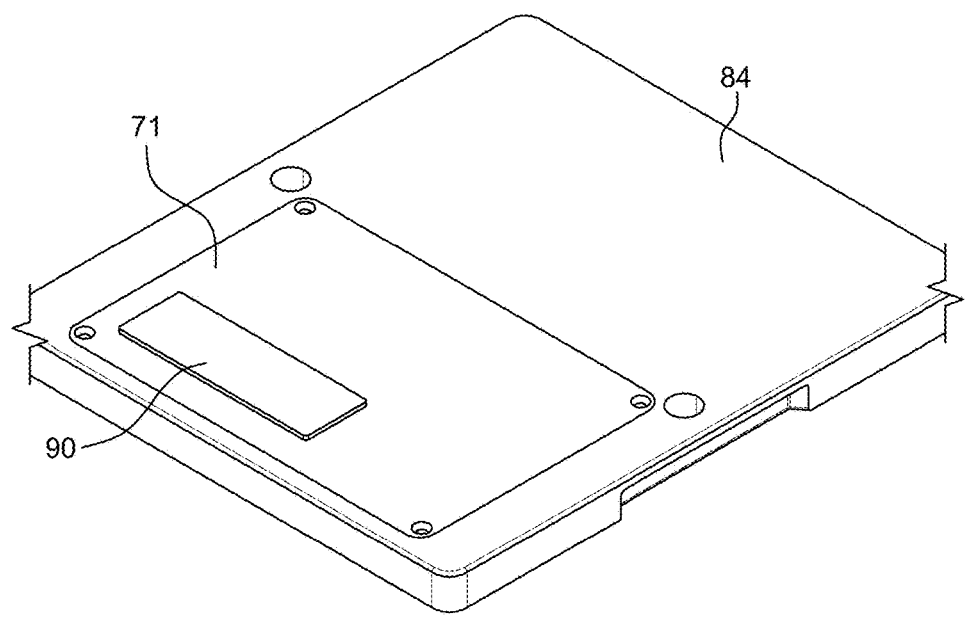
FIG. 4e is one embodiment a tray that can rest on a drawer base in accordance with some embodiments of the presently disclosed subject matter.
Figure 4F:
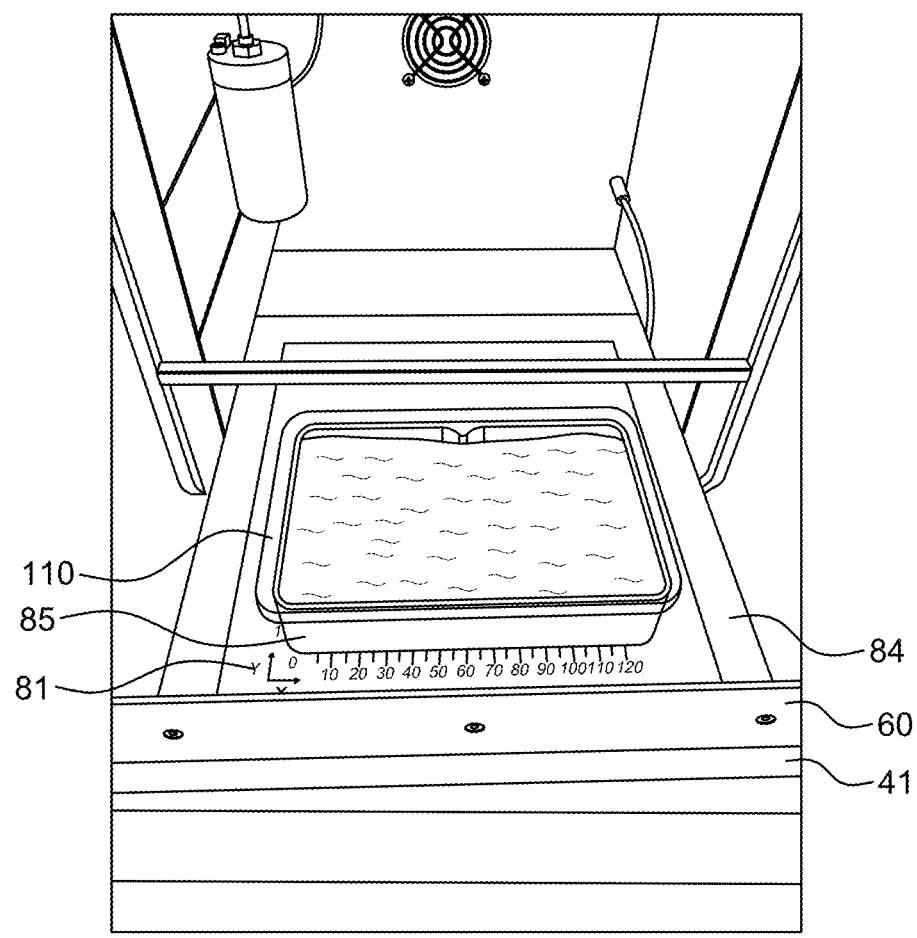
FIG. 4f is a front plant view of a humidity chamber positioned on a drawer in accordance with some embodiments of the presently disclosed subject matter.
Figure 4G:
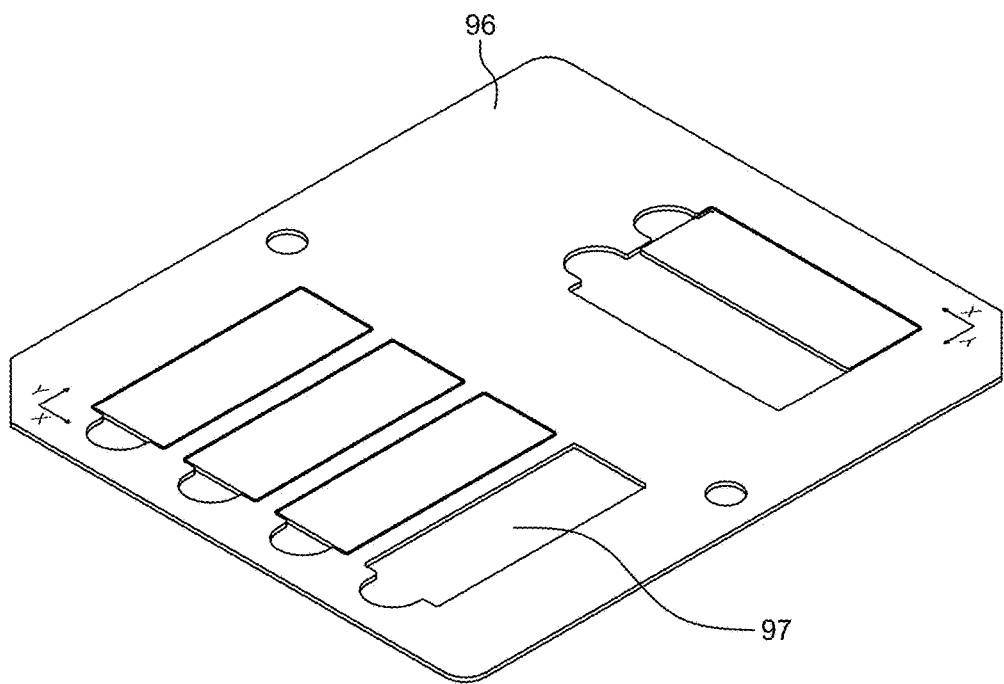
FIG. 4g is a perspective view of a positioning plate in accordance with some embodiments of the presently disclosed subject matter.
Figure 4H:
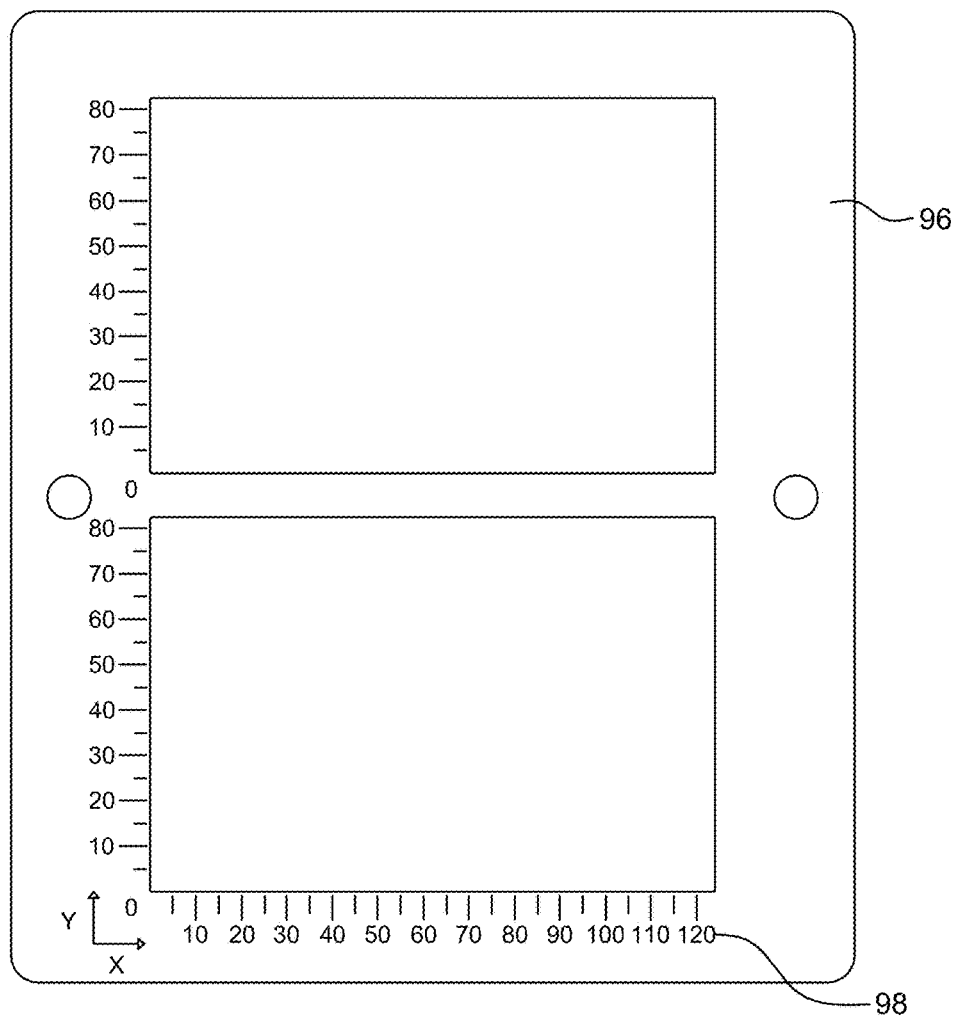
FIG. 4h is a top plan view of a positioning pate in accordance with some embodiments of the presently disclosed subject matter.

FIG. 4d illustrates one embodiment of tray 84 that can be configured to rest on and/or be removably attached to drawer base 80. As shown, in some embodiments, the tray comprises positioning plate 81 that can include one or more indicia that allow the user to make various measurements, such as (length, width, and the like) and/or to properly position the medium. For example, the dimensions of medium 90 can be easily determined using indicia 82. It should be appreciated that in some embodiments, tray 84 can be a heated or cooled tray. For example, as illustrated in FIG. 4e, tray 84 can include heated or cooled plate 71 positioned below medium 90. FIG. 4f illustrates one embodiment of humidity chamber 85 positioned on heated tray 84. As shown, the tray can include plate 81 comprising indicia 82 to ensure that the humidity chamber is centered and/or properly positioned. FIG. 4g is one embodiment of a positioning plate that can be used. For example, positioning plate 96 includes one or more inserts 97 that function as predetermined positions for equipment, such a medium slide. In some embodiments, the positioning plate can include position measurements 98, as shown in FIG. 4h.

Figure 5A:
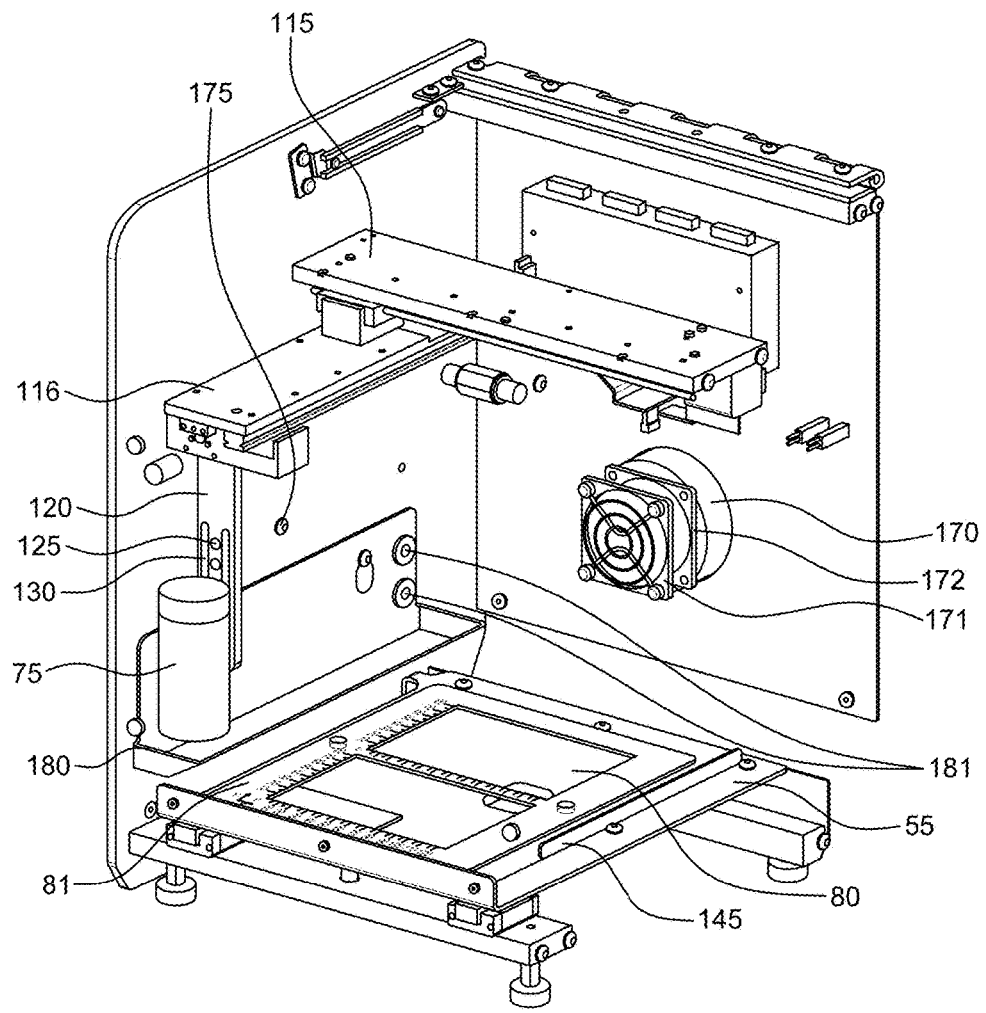
FIG. 5a is a perspective view of the interior of a chemical deposition system with exterior panels removed in accordance with some embodiments of the presently disclosed subject matter.

FIG. 5a depicts a cutaway view of sprayer 10 with top panel 15, bottom panel 20, one side panel 25, front viewing panel 40, and front panel 30 removed. As shown, spray assembly 75 for depositing the chemical layer onto medium 90 is viewable. In some embodiments, the spray assembly can comprise x-axis arm 115 positioned perpendicularly to and coupled with y-axis arm 116 to allow the spray assembly to move in at least two perpendicular directions. Thus, the spray assembly 75 can be coupled to X-axis arm 115 and/or y-axis arm 116. In this way, the spray assembly can be maneuvered with respect to medium 90. In some embodiments, both the spray assembly and the medium can change position. In some embodiments, only one of the spray assembly or the medium can change position.

Any of the wide variety of known inputs, algorithms, and/or programming can be used to control the movement of the spray assembly in relation to the X and Y-axis arms 115, 116. For example, spray assembly 75 can be translated in relation to the Y-axis arm and the Y-axis arm can be translated in relation to the X-axis arm. To this end, gears, motors, tracks, and/or guides can be provided to effect movement of the spray assembly and/or arms 115, 116. In some embodiments, one of X-axis arm 115 or Y-axis arm 116 can remain in a static position. In some embodiments, axis engagement 120 can be positioned between, and engaged with, the spray assembly and the axis arms for coupling the spray assembly to one of the arms. The spray assembly can be coupled to the engagement axis using any suitable method, including (but not limited to), the use of mechanical elements, adhesive, snap-fit arrangements, and the like. For example, as shown in FIG. 5a, the engagement axis can include one or more engagement apertures 125 for permitting coupling to the spray assembly at a fixed height from medium 90. In some embodiments, engagement tracks 130 can be provided for permitting translation of the spray assembly between various heights. Automatic and/or manual controls can be provided for adjusting the height of the spray assembly.

FIG. 5a also illustrates one embodiment of sample drawer 55 including plate 81 affixed to drawer base 80. The alignment plate can include one or more cutouts in any desired shape for positioning medium 90 therein. In some embodiments, the plate can include one or more markings that can indicate a measurement, the boundaries of medium 90, and the like. However, it should be appreciated that in some embodiments plate 81 can be configured without apertures and/or markings. In some embodiments, the system can include one or more ridges 145 for positioning medium 90. To this end, the plate can be removable from base 80 to permit the interchange of differing alignment plates and/or to rotate a plate to a different orientation. Advantageously, drawer 55 permits the user to slide plate 81 for a closer and more perpendicular view of the placement of the medium.

In some embodiments, one or more inserts can be positioned on or removably attached to drawer base 140. The inserts can be configured in any desired any shape and size. For example, an insert can be placed between base 140 and alignment element 135 to adjust the height and/or angle of medium 90 relative to the spray assembly. An insert can also serve as a mask to prevent the deposited chemicals to reach certain area of the medium. In some embodiments, the insert can include a heater, a cooler, and/or a sensor. To this end, any desired number of sensors can be provided throughout the disclosed system for measuring and/or detecting one or more parameters. For example, suitable parameters can include (but are not limited to) air temperature, ejected fluid temperature, ejected gas temperature, chemical layer temperature, deposited fluid temperature, medium temperature, base temperature, pressure, wetness or dryness of the chemical layer, wetness or dryness of the deposited fluid or medium, humidity, and/or evaporation rate. Such sensors are standard and are known to those of skill in the art.

The sprayer internal compartment can include one or more apertures 175 for permitting gas and/or fluid flow from externally positioned gas and fluid reservoirs. In some embodiments, the gas and/or fluid reservoirs can be housed within interior compartment 45. The gas and fluid apertures can extend through any of the panels of the enclosure. For example, in the embodiment illustrated in FIG. 5a, apertures 175 extend through left side panel 25.

In some embodiments, the disclosed system can include a fan. For example, a fan venting the interior compartment to outside the assembly can be set to turn on and off to increase or decrease the air flow and air recycling, and/or control the humidity level in the proximity of the medium. In some embodiments, the interior compartment can be connected to an air conditioning system and can provide even greater control of temperature, humidity, and/or pressure inside the compartment. For a given fluid, temperature, humidity, and/or pressure can directly affect the evaporation rate, which is especially important for fluids with a high aqueous content with an evaporation rate that can be greatly reduced in humid environments. For example, the stability of trypsin digest protocols would be affected in environments with insufficient air-conditioning and in environments wherein the moisture level varies greatly between summer and winter.

Figure 5B:
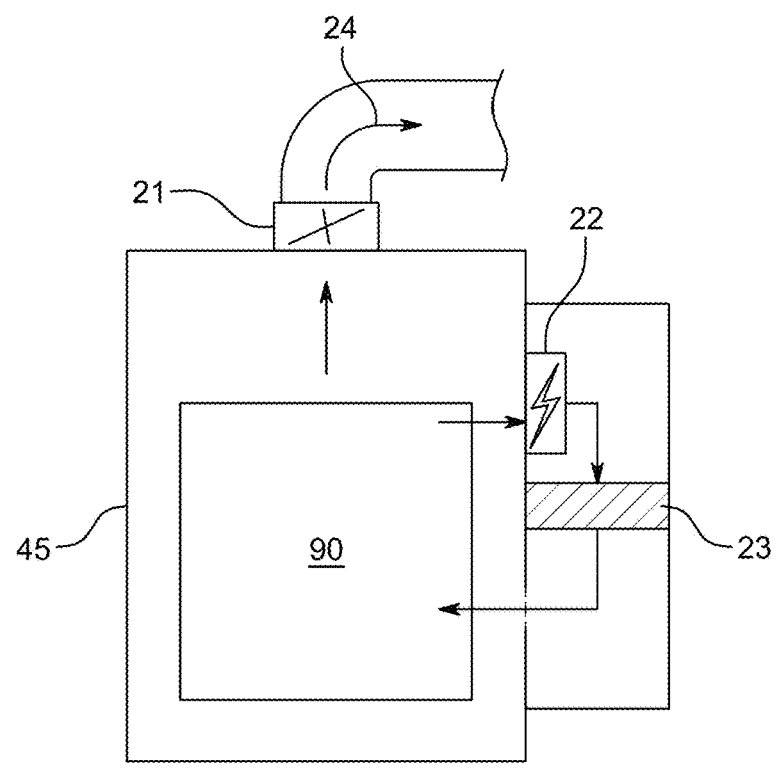
FIGS. 5b and 5c are front plan view of chemical deposition systems comprising one or more air conditioning units.

FIG. 5b illustrates one embodiment of system 5 that includes an air conditioning unit to directly control the temperature, humidity, and/or pressure of interior compartment 45. Particularly, as shown, the interior compartment comprises first vent 21, which in some embodiments can be a fan positioned on the rear panel in communication with exhaust 24. The first vent can be operated constantly or intermittently. The interior compartment further includes second vent 22, which in some embodiments can be a fan positioned on a side panel. The vents recycle air through desiccant 23, which can be configured as a desiccant bed or a cartridge in some embodiments. Any suitable desiccant known or used in the art can be used, including (but not limited to) silica, calcium oxides, metal silicates, activated alumina, activated carbon, molecular sieves, and combinations thereof). In this way, dry air is recycled within the interior compartment, as indicated by the arrows. It should be appreciated that any number of vents can be used and can be positioned on any desired surface of the disclosed system.

Figure 5C:
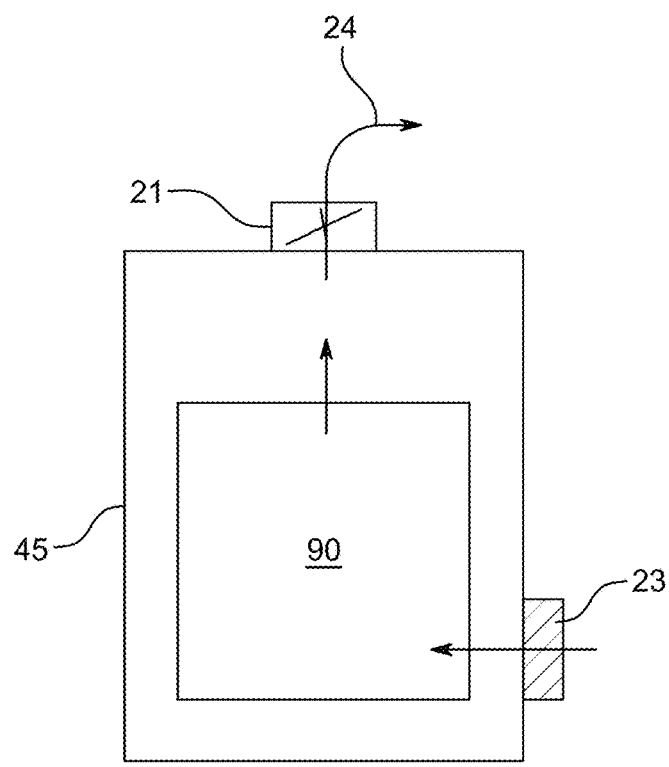

FIG. 5c illustrates an alternate embodiment of a system that includes an air conditioning unit. Particularly, the interior compartment includes first vent 21 (which can be a single fan) that draws air outside and creates a depression inside enclosure 45 that is sufficient to draw in fresh air that passes through desiccant 23, as shown by the arrows. The system of FIG. 5c requires only a single fan and a properly sealed interior enclosure.

As shown in FIG. 5a, interior compartment 45 can include gutter 180 positioned on one of the two opposing side panels for collecting fluid. Alternatively, gutter 180 can be selectively fastened or coupled to any of the panels of the enclosure. In some embodiments, additional gutters 180 can be provided for one or more of the panels of the enclosure. In some embodiments, the one or more gutters can be translatable in relation to a respective panel for permitting fluid to be collected when the fluid is sprayed towards a portion of drawer base 80 not covered by medium 90. In some embodiments, gutters 180 can collect fluid when the spray assembly is in a resting position. The gutters can include gutter apertures 181 for permitting gas and fluid flow therethrough.

Figure 6A:
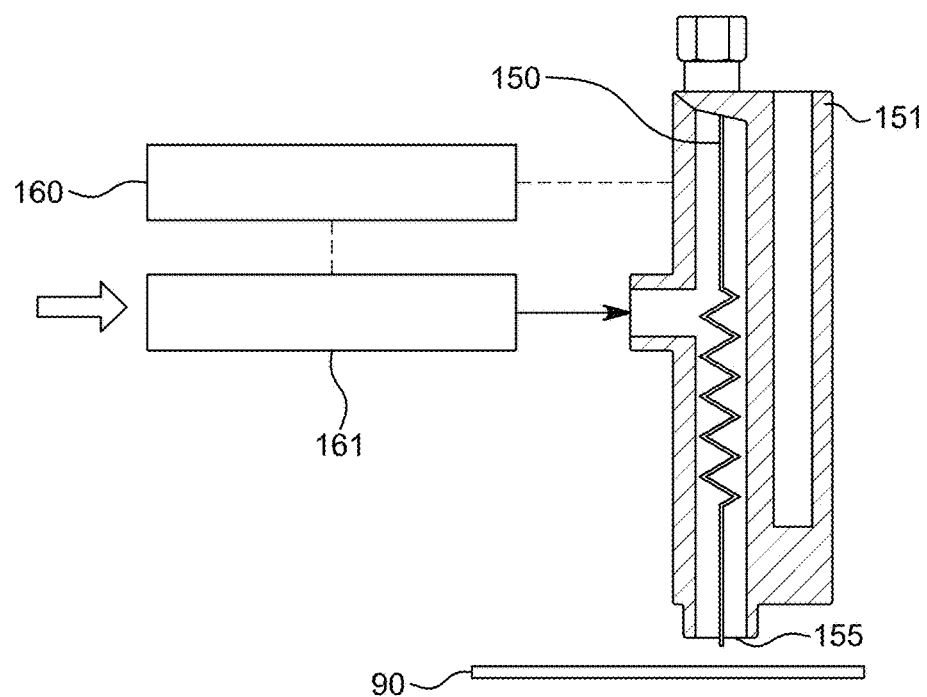
FIGS. 6a-6c are front plan views of a sprayer nozzle in accordance with some embodiments of the presently disclosed subject matter.

As shown in FIG. 6a, spray assembly 75 can include nozzle 151 that comprises capillary 150 for receiving and ejecting a fluid from exit 155 to form a chemical layer upon medium 90. Representative gases that can be received and/or ejected can include (but are not limited to) ambient air, nitrogen, and/or helium. Representative fluids that can be received and/or ejected can include (but are not limited to) waters, methanol, ethanol, acetonitrile, acetone, and/or chloroform. In some embodiments, the disclosed system can comprise temperature controller 160 to heat (or cool) capillary 150, nozzle 151, exit 155, the fluid, and/or the gas. In some embodiments, the temperature controller can include a gas spray heater and a fluid spray heater, each being independently operable for independently controlling the heat of the gas and fluid. The spray heater can work in conjunction with an external heater for heating the fluid and/or gas before each is received by the spray assembly. See, for example, U.S. Pat. No. 5,772,964, incorporated by reference herein. In some embodiments, air or liquid can be preheated using preheater 161, as shown in FIG. 6a.

Figure 6B:
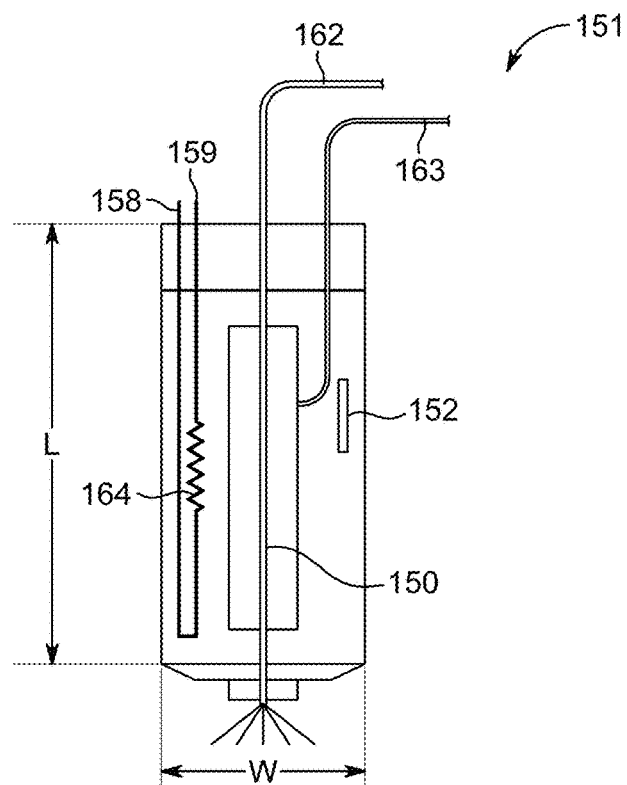

FIG. 6b illustrates one embodiment of nozzle 151 comprising capillary 150 and temperature sensor 152. Fluid inlet 162 provides the source of capillary fluid, as shown. In addition, the spray nozzle can include gas inlet 163 which can include any desired gas. The nozzle further includes heat exchanger 164. In some embodiments, the nozzle can have a length L of about 3.5 inches or less, such as about 3.5, 3.4, 3.3, 3.2, 3.1, 3.0, 2.9, 2.8, 2.7, 2.6, 2.5, 2.4, 2.3, 2.2, 2.1, 2.0, 1.9, 1.8, 1.7, 1.6, or 1.5 inches. In some embodiments, the nozzle can have a length of about 3-3.75 inches. In some embodiment, the nozzle can have a width W of less than about 1.75 inches, such as about 1.75, 1.7, 1.65, 1.6, 1.55, 1.5, 1.45, 1.4, 1.35, 1.3, 1.25, 1.2, 1.15, 1.1, 1.05, or 1.0 inches. Thus, the nozzle can have a length of less than 3.5 inches and a width of less than 1.75 inches. However, smaller or larger nozzles are also included within the scope of the presently disclosed subject matter.

Figure 6C:
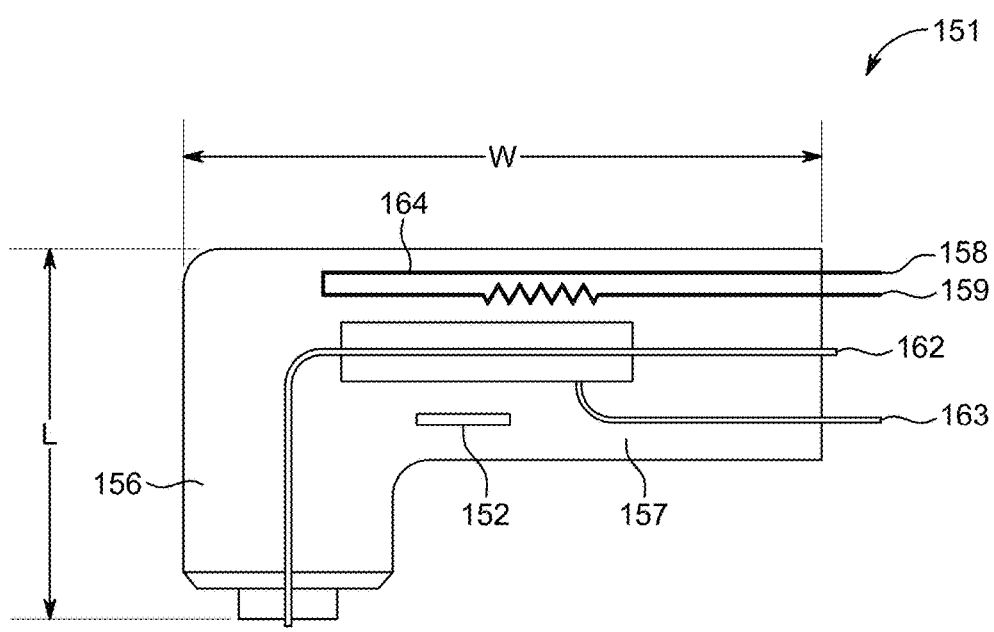

FIG. 6c illustrates an alternate embodiment of spray nozzle 151. Particularly, in some embodiments, the nozzle can be angled to half the height of standard nozzles. In some embodiments, the angled nozzle can have first and second arms 156, 157 joined at an angle of about 90 degrees, although the presently disclosed subject matter is not limited and the arms can be joined at any angle. FIG. 6c further illustrates gas inlet 163, fluid inlet 162, and heat exchanger 164. Heater 158 and power inlet 159 are also shown. In some embodiments, first arm 156 can have a length L of about 1.75 inches (e.g., 0.75-2.0 inches) and second arm 157 can have a width W of about 3 inches (e.g., 2-4 inches). However, smaller or larger nozzles are also included within the scope of the presently disclosed subject matter.

Advantageously, a smaller nozzle with a lower mass would be appropriate for velocities higher than about 5,600 mm/min would allow the user to further benefit from flow linear flow rate. Also, a nozzle with a smaller total height would necessitate a smaller housing and enclosure. As a result, further miniaturization of the system can be enabled.

In some embodiments, multiple spray assemblies can be provided and/or multiple capillaries 150 and/or nozzles 151 can be included on one or more spray assemblies. For example, a second capillary and/or second spray assembly can enable a second fluid to be sprayed for interacting with the chemical layer being formed by the first fluid. Similarly, a second nozzle and/or spray assembly can enable second gas to be sprayed. The additional capillaries, nozzles, and/or assemblies can permit simultaneous spraying with the original spray assembly 75 and/or pre/post-spray treatment of medium 90 and/or a chemical layer.

In some embodiments, spray heater 158 can be an infrared heater for accelerating drying or evaporation. Controlling the evaporation rate of the fluid while being ejected from capillary 150 and/or while resting upon medium 90 can affect the 'wetness' or 'dryness' of the chemical layer being formed by the components of the fluid. The uniformity of the height, width, and/or structure of the chemical and/or the constituent rows or columns of the chemical layer as fluid is applied to the medium can also be affected by evaporation rates of the fluid. To further control evaporation, drawer base 80 can include heater element 70 to heat the drawer base and/or medium 90, as described herein above. The medium heater, spray heater, and/or external heater can be controlled automatically (via inputs, algorithms, and/or programming), using manual input, and/or by physical manipulations of controls located in the system.

Evaporation rates can also be controlled by the flow of air within interior compartment 45 of sprayer 10. FIG. 5a depicts fan positioned on and through rear panel 35 for exhausting air from the enclosure interior. It should be appreciated that fan 170 can be positioned on and through any panel of the enclosure. In some embodiments, the fan can be configured to include housing 171 for safety and/or vent 172 for filtering (e.g., particulate air) or for absorbing (e.g., charcoal filter) the air during fan exhaust. In some embodiments, fan 170 can be selectively engaged or coupled to a duct to contain and/or direct flow of the exhausted air. By providing a vent and/or duct, the disclosed system can be used in accordance with safety regulatory schemes without the need for a vented hood.

One or more tubes can house and direct flow of gas and/or fluid from the reservoirs to a spray assembly that includes spray nozzle 75. In some embodiments, the tubes can include one or more sections having a connection between the sections. When fluid and/or gas flows through an aperture of an enclosure panel and/or a gutter aperture, the flow can pass from one section, through one or more connections, to another section. Upon disengagement of a section from one of the connections, the fluid housed within the tubes can be collected by gutter 180. Additionally, the gutter can collect fluid expelled from the tubes during any ejectment, cleaning, and/or sterilization processes. The gutters can be coupled to a drain line for permitting any collected fluid to flow to a collection reservoir. The collection reservoir can be positioned within the enclosure or can be external to the enclosure.

The connections, the sections of the tubes proximal the connections, and/or any other section can include one or more filters for filtering contents of the fluid and/or gas flow within the tubes. In some embodiments, the filters can be positioned within or proximal to gutter aperture 181 for permitting cleaning and/or interchange of the filters while collecting any fluid expelled during the cleaning or interchange.

The tubes can also include a switching valve along the length thereof to control the flow of fluid and/or gas between the tubes, and/or for controlling the type of fluid and/or gas flowing therethrough. In some embodiments, one or more switching valves can be activated for permitting manual or automated ejectment and/or conditioning or washing processes. For example, selector valve 52 can be used to alternate the source fluid of a tube between a fluid containing components for forming a chemical layer to a fluid for conditioning or washing the tube and/or capillary of the spray assembly. In some embodiments, an injection valve can serve as a chemical solution reservoir. In some embodiments, a 2-way valve can be used to switch the flow from two or more alternative pump flow feeds.

Figure 7A:
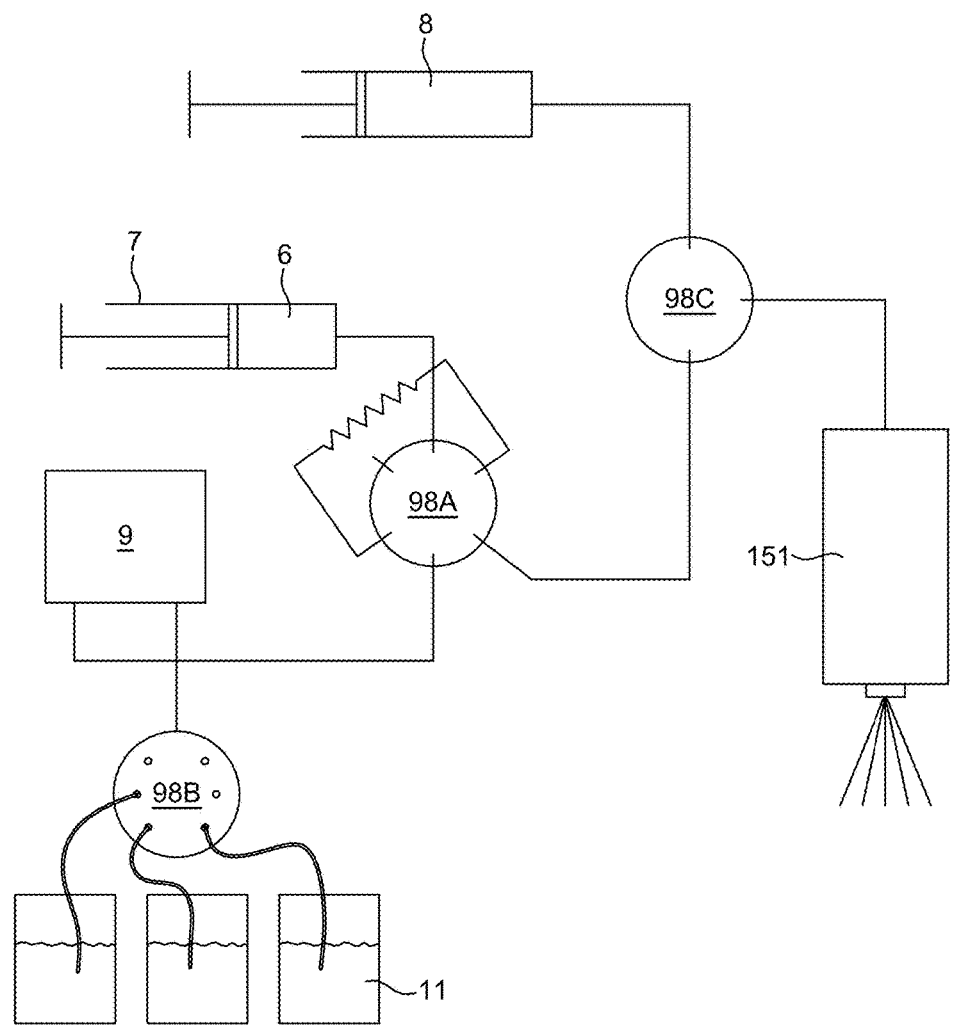
FIGS. 7a-7c are representations of various switching valve arrangements in accordance with some embodiments of the presently disclosed subject matter.

FIG. 7a illustrates one example of switching valves 98 shown in arrangement to achieve automated transition from one liquid to another without interruption of spray or loss of chemicals. Particularly, as shown valves 98 can be 2, 3, 4, 5, 6, 7, 8, 9, or 10-port valves, selector valves, or combinations thereof. For example, the valves can include injection valve (6-port) 98a that allows input of matrix 6 from applicator 7. In some embodiments, the applicator can be a syringe. The system can also include selector valve 98b in fluid connection with one or more reservoirs 11 that house one or more fluids (e.g., matrix, enzyme, washing fluid). The disclosed system can also include two-way valve 98c that allows the input of enzyme solution 8 from applicator 7 and distributes the solution to an injection valve and/or directly to nozzle 151. One or more pumps 9 can affect the flow of materials to and from the valves.

Figure 7B:
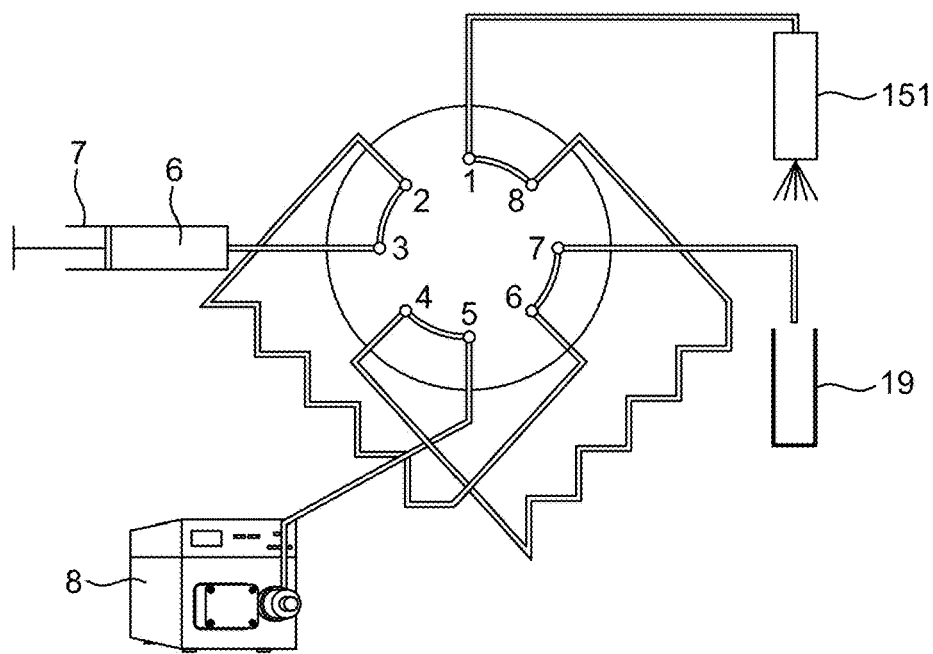
Figure 7C:
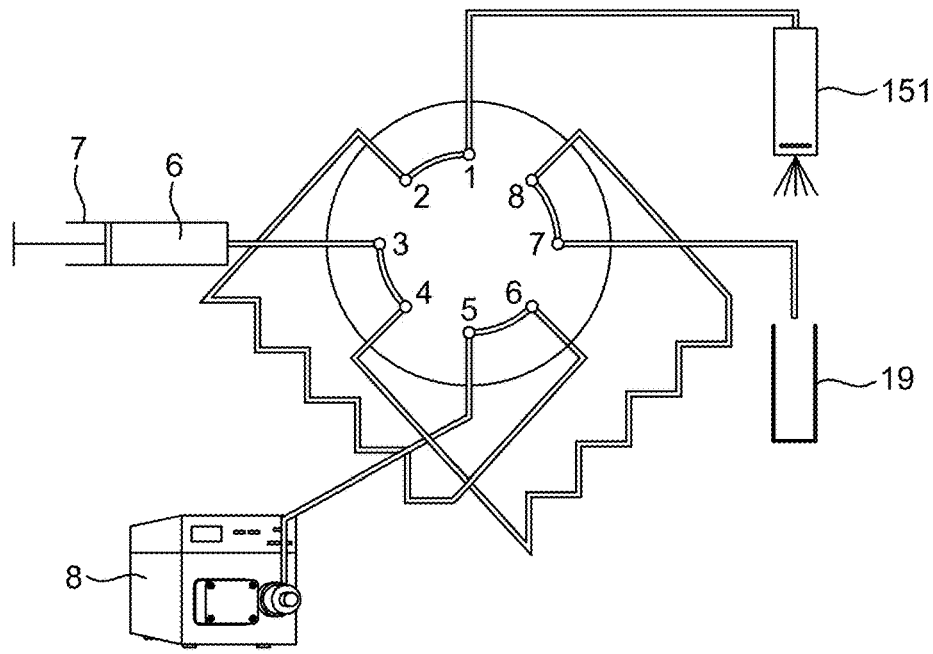

In some embodiments, the switching valves can be configured as eight port valves with 2 loops as illustrated in FIGS. 7b and 7c. Particularly, matrix 6 and/or solvent 18 can be loaded into the switching valves and can be routed to spray nozzle 151 and/or waste 19.

The disclosed system can include one or more pumps to control the flow of fluid and/or gas. In some embodiments, the pumps can be used for degasification of the fluid as it flows. Degasification can be accomplished by purging the fluid at a high rate and/or by maintaining a constant flow of the fluid at a low rate over a set period of time.

In use, the disclosed system automatically or manually translates spray assembly 75 into patterns for providing a uniform chemical in relation to the matrices. The pattern of deposition of the fluid upon medium 90, the velocity of the translation and/or spray, and the spacing between tracks of the pattern can substantially affect the uniformity (or homogeneity) and structure of the chemical and its subsequent analysis. One exemplary spray pattern includes chemical deposits spaced 1/n apart, where n can equal any integer one or greater. Delayed timing between the deposit of tracks (e.g., rows or columns on the medium) can permit previously deposited tracks to dry or evaporate. In some embodiments, several wide tracks can be deposited and interspersed with smaller tracks there between. Tracks can overlap when deposited, can be spaced apart, or both. The velocity of the spray assembly can be adjusted during and/or between track deposition. One or more sensors can be employed to automatically or manually adjust track deposition as desired.

Therefore, the disclosed system provides novel spray patterns for more homogenous deposition (smoother peaks and valleys) compared to prior art systems. Particularly, the disclosed system can produce a meshing pattern using fractional deposition offsets at 1/n track spacing with alternate rotations (e.g., using deposition at ½, ⅓, ¼, ⅔, ¾, and the like track spacing). Combinations of wide track spacing (>8 mm) and fractional deposition offsets can be used to maximize the time between overlapping tracks (e.g., track spacing of 20 mm and offsets of 0, 5, 10 and 15 mm for a total of 4 non-overlapping passes).

Figure 8A:
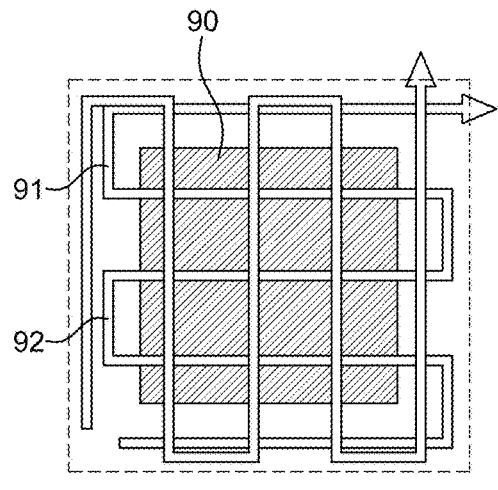
FIGS. 8a-8f are top plan views of various spray patterns that can be used to spray a medium in accordance with some embodiments of the presently disclosed subject matter.
Figure 8B:
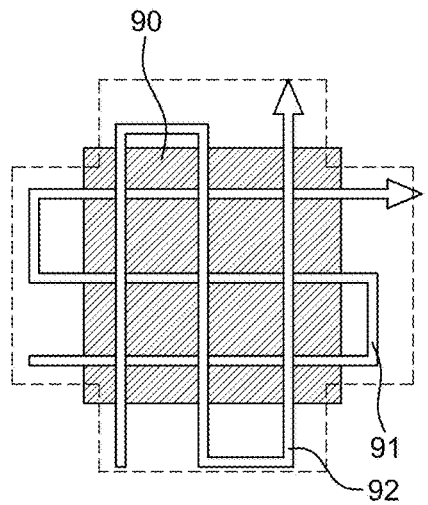
Figure 8C:
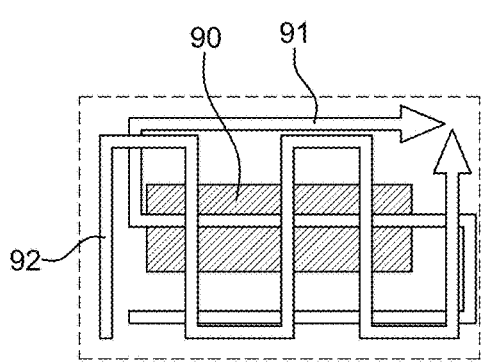
Figure 8D:
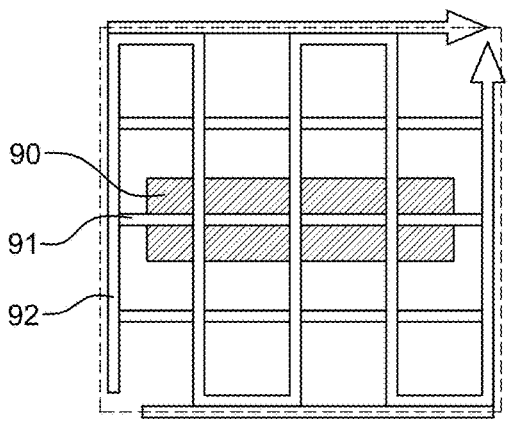
Figure 8E:
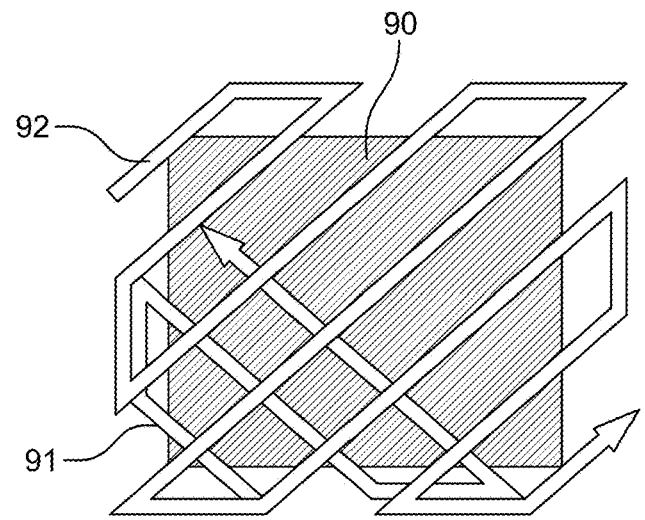
Figure 8F:
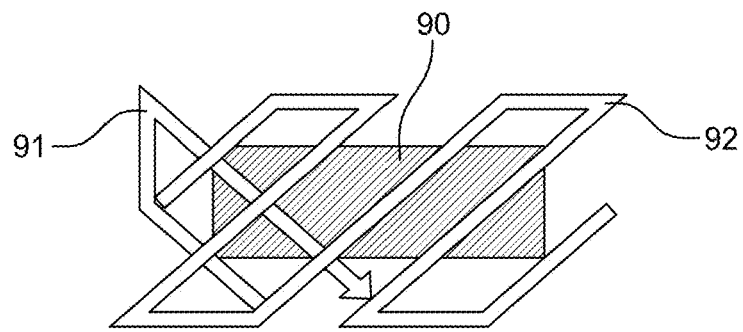
Figure 8G:
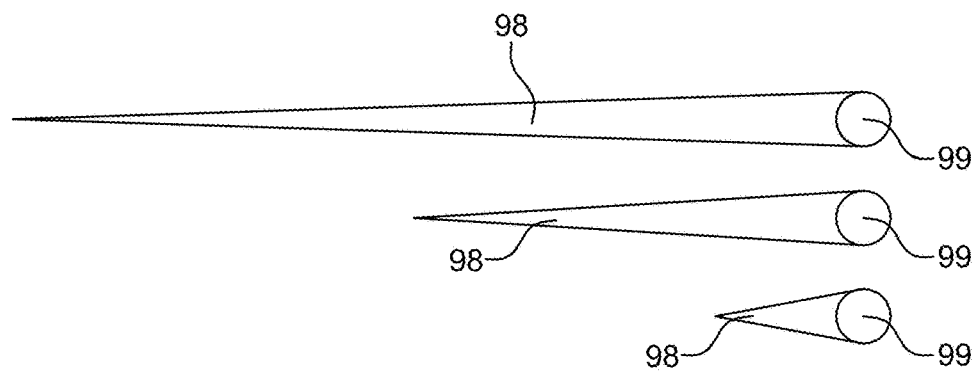
FIG. 8g is a representation of three comet trails of varying lengths in accordance with some embodiments of the presently disclosed subject matter.

The disclosed system further provides novel spray patterns for eliminating long side/short side bias. Particularly, the system can include an automatic expansion of the spray area from one shape to another (e.g., rectangle to square). The system can further enable a diagonal pattern to cover rectangles. The system can include a Swiss Cross spray pattern, providing overspray only along the spray length (not width) to reduce chemical consumption. FIG. 8a illustrates one embodiment of a square or rectangular spray pattern that can be used to spray medium 90. For example, the spray pattern can include both horizontal 91 and vertical 92 spray paths. FIG. 8b illustrates one embodiment of a Swiss Cross pattern that can be used. For a given medium size, the Swiss cross pattern delivers the same amount of spray on the medium but cuts the length of the spray path about in half compared to conventional spray paths, thereby reducing the amount of fluid required in half. FIGS. 8c and 8d illustrate a rectangular spray pattern and an automatic square pattern, respectively. When medium 90 is longer on one axis, the shorter spray tracks overlap before they are completely dry. To avoid this, the presently disclosed system can include software that automatically selects a square pattern that covers the medium without creating a bias in the drying rate. FIGS. 8e and 8f illustrate two embodiments of diagonal spray patterns that can be used. A diagonal flow path does not create bias between the short side and the long side of a rectangular medium. As a result, the spray dryness is homogeneous in both direction when the medium is both square and rectangular-shaped.

The disclosed system can automatically calculate wait time (using an algorithm, for example) at the end of a track to equalize travel time in both directions. In some embodiments, a sensor can be used to measure the spray evaporation speed. In addition, comet trail length can be measured, shine on spray can be visualized, and heat loss from evaporation speed can be measured. The term "comet trail" as used herein refers to the wet trail 98 of undried spray that follows the spray path 99, as shown in FIG. **8*g***. The phrase "shine on spray" refers to the ability to determine whether the spray has dried based upon the appearance of a shine to the spray when wet. The data can be used to guarantee process stability for multiple sample types and sizes. Further, a sensor can be used to measure gas pressure variation during a spray sequence and/or fluid pressure.

The disclosed system enables increased spray nozzle velocity that has been tested up to about 5,600 mm/min and can be configured to achieve even higher velocity (e.g., up to about 18,000 mm/min). Thus, the disclosed system can include a maximum nozzle velocity of about 18,000; 17,500; 17,000; 16,500; 16,000; 15,500; 15,000; 14,500; 14,000; 13,500; 13,000; 12,500; 12,000; 11,500; 11,000; 10,500; 10,000; 9,500; 9,000; 8,500; 8,000; 7,500; 7,000; 6,500; 6,000; or 5,600 mm/min. In combination with fluid flow rate, the spray nozzle velocity determines how much fluid is deposited on a given surface area during the spray nozzle movement over the medium. Linear flow rate (LFR), defined as the ratio of the fluid flow rate (ml/min) by the spray nozzle velocity (mm/min) (measured in ml/mm) provides a way to compare the dryness or wetness of different protocols.

LFR (ml/mm)=Fluid Flow Rate (ml/min)/(Nozzle Velocity (mm/min)

In the disclosed system, the ratio can be automatically calculated. There can be three ranges for the spray quality from "wet" to "dry" to "super dry" spray conditions. When the LFR is greater than 0.000083 ml/mm, the spray conditions are considered "wet" spray conditions. When the LFR is between 0.000083 ml/mm and 0.0000083 ml/mm, the spray conditions are considered "dry" spray conditions. When the LFR is less than 0.0000083 ml/mm, the spray conditions are considered "super dry" spray conditions.

In some embodiments, the user can select a desired dryness level, and the system can decide flow rate and velocity automatically. The system can calculate the LFR (simple) or the system can include a sensor to measure the spray dryness and adjust the flow rate and velocity to achieve a set spray quality.

Increased stage velocity is of great interest as it expands the range of protocols that can be generated on the disclosed system.

At a constant LFR, the higher velocity offers the ability to create a drier spray including super dry conditions. Advantageously, the super dry conditions can be used to deposit difficult-to-dry solutions such as matrices forming hydrates (see Example 3 herein, where velocities of 2,000 and 3,600 mm/min were used to deposit and successfully dry THAP matrix, a solution known to form hydrates that are very difficult to dry). Super dry conditions can also be used to create smaller MALDI matrix crystals at practical flow rates (e.g., above about 0.050 ml/min), further decreasing the size of matrix crystals compared to Tech Note 34. Further, super dry conditions can reduce the need for a highly volatile solvent, which are typically less environmentally friendly (e.g., acetone, chloroform), as presented in Example 5 here (where a protocol using 67% chloroform was replaced by a protocol using only 50% chloroform with the same data quality).

At constant LFR, the higher velocity offers the ability to increase fluid flow rate in step with velocity, resulting in a similar spray quality using protocols as much as 3× faster (as presented in Example 2 herein, where a standard protocol using flow rate of 0.100 ml/min, velocity of 1,200 mm/min, and of duration 13.20 minutes was substituted by a new protocol with a flow rate of 0.300 ml/min, velocity of 3,600 mm/min, producing the same quality of data 3× faster.

It is noted that existing systems having maximum spray nozzle velocity of 2,000 mm/min, can only produce a super dry condition if the fluid flow rate is set below 0.016 ml/min, which is not practical and would make the sample preparation duration both lengthy (more than 30 minutes) and more prone to spray clogging (multiple clogging per week based on daily operation) due to the slow-moving fluid.

For small spray areas (where spray returns sooner to same location) higher stage velocity can be used in conjunction with wait time to allow more drying between passes. Wait time can be automatically calculated (e.g., using an algorithm) to keep the dry/wet effect the same regardless of sample area size and shape. Track spacing can be increased from 1 to 3 mm (standard) to more than spray width (5 to 10 mm) to ensure non-overlap of spray. Homogeneous coating can be achieved through use in conjunction with novel spray meshing patterns. Optimum flow rates, patterns, velocity, and wait times for the same wetness or dryness can be automatically calculated (e.g., using an algorithm).

Further, the disclosed system can be used to control the chemical solution pressure to allow a high nozzle temperature. For example, if there is pressure within the interior of a capillary, the nozzle can be at a higher temperature than ambient pressure boiling point. Solvent degassing can address instability (e.g., puffing issues). In addition, pressure regulators can be used on the solvent line. Longer or lower I.D. (internal diameter) capillaries can be used to create a higher pressure inside the nozzle head. The spray chamber pressure can be controlled to allow for faster evaporation rates. For example, a vacuum pump can be connected to the chamber to create a low-pressure atmosphere above a sample. A high velocity fan can be used to vent the chamber and create low pressure. Other elements can be provided to decrease pressure by fast draft.

In the disclosed system, sample temperature can be controlled to counteract sample surface cooling. For example, spray chamber temperature can be controlled with an auxiliary heater positioned inside the chamber. Sample holder temperature can further be controlled (using a heated film, hot water heater, etc.) to compensate for evaporative cooling. Samples can be warmed above ambient temperature to accelerate evaporation. Further a warming lamp (infrared or other light energy) can be installed to keep sample surface warm and/or to further accelerate drying. Current intensity (amps) can be measured to calculate cooling rate induced by evaporative cooling.

The above aspects can be used to increase drying speed and allow use of more environmentally-friendly solvent solutions compared to prior art systems. For example, as set forth below in Example 5, a 1:1 solution of chloroform: methanol can be used in place of a 2:1 solution of chloroform, hence reducing by 24% the amount of chloroform used, while achieving the same or similar dry effect and small crystal size.

Further, the sliding drawer described above allows for visualization of a sample with no viewing angle bias. In addition, the drawer allows for easy and quick positioning, taping of edges, and dismount of sample. Further, the disclosed drawer protects users from the heated nozzle, which can be a safety hazard. Due to the drawer, there is no need to remove a sprayer panel each time, which can be dangerous as well as time-consuming. The drawer enables a smaller instrument footprint (e.g., no need to allow room for hands inside the chamber). The disclosed drawer further provides for a dual level sample holder to allow one position for an enzyme digest and one position for chemical deposition. Heated drawer embodiments can comprise a heated plate inserted in the sample drawer or an external unit to allow removal of low boiling point solvents or wax. For example, an 80° C. plate can be used to remove paraffin from paraffin-embedded tissues.

The disclosed humidity chamber covers the medium with a chamber that comprises a liquid reservoir and a suspended tray to receive a sample. The chamber further creates a warm and humid atmosphere optimum to certain in-situ chemical reactions, such as enzymatic digestion. The chamber also allows for rehydration of a sample and further control of the crystal size and/or chemical layer penetration and interaction with the sample.

The disclosed solvent delivery module can allow for automatic dispensing, unattended operation, automated start and shut down. The delivery module further allows for multi-spraying sequences, such as one more passes with a first solution, followed by one or more passes with a second solution. Alternatively, one or more passes with a first solution can be made, followed by a rehydration step. Further, a digestion pass can be made (e.g., trypsin digestion) followed by a chemical deposition.

The disclosed solvent delivery module can also be configured with a multiple loop switching valve. In some embodiments, an 8-port valve with a small 0.5 ml loop to store a solution (e.g., a trypsin solution) and a large 5 ml loop to store a matrix solution (e.g., a MALDI matrix solution) can be used, providing the advantage of both low volume and large volume dispensing with a single pump system, and without having to reconfigure loops or push syringe size between different chemicals.

The dual temperature nozzle provides a nozzle with a shorter or longer liquid path (shorter or longer capillary), combined with a shorter or longer nebulizing gas flow path (shorter or longer gas flow path). The nozzle can be constructed from a material designed to increase or decrease the heat exchange between heater cartridge and medium. Such materials are well known those of ordinary skill in the art. For example, in some embodiments, the spray nozzle can be constructed from a lightweight material. For example, the nozzle can include an aluminum core with one or more ribs, using less metal but allowing for better heat exchange. Different materials with lower weight and higher heat conductivity can also be used. A low-weight nozzle allows for faster operation of the stage without tasking the motorized XY stage, as well as easier inclusion of the spray technologies on other robotic platforms with a light duty robotics mechanism.

The disclosed multiple spray head nozzle can deposit a solution that enhances extraction (e.g., MALDI chemical spray followed by chloroform spray to extract lipids preferentially). For example, a dual spray head can be used with a secondary drying spray (nitrogen flow only). Multiple spray heads can be used to achieve other combinations of pre-spray and post-spray treatments. In some embodiments, the spray head can include an infrared heater or other energy source capable of accelerating drying or extraction.

The small spray nozzle allows the design of a smaller footprint system. In addition, the small nozzle is easier to migrate to other existing robotic platforms (e.g., Tecan Workstation, CTC System, etc.).

The solvent lines can be degassed for higher temperature operation. For example, once degassed, the solvent in the capillary can be heated above its boiling point without becoming unstable (puffing). Thus, a degasser can be included in the liquid flow path. Further chemical can be filtered through a high backpressure frit to decrease gasses dissolved. The pumping procedure can degas solvent as it flows. Aspects can include purging at high flow rate, and constant flow at very low flow over night to keep system pressurized.

The disclosed system can further include a tray holder for easier sample loading, more precise alignment of target, and safer operation (e.g., the user will no longer put their hands inside the chamber for loading). Double heater controls provide for one for the nozzle and one for the tray holder. A 4× faster nozzle speed thanks to lighter weight XY stage and new type of bearing is provided. Control of external pump, smart gutter design for easier clean up and access to filter replacement, and pull out tray that eliminates the need to remove glass panel to load samples and provides easier visual alignment. Additionally provided are multiple height with inserts on drawer, a narrower format for decreased space usage, and an open top for easy servicing. This advantageously allows for easier replacement of electronics if needed, easier access to liquid connections, and easier access to filter for cleaning. A serial port out is provided to pump for integrated control of external pump. Advantageously, this connects to another pump which has switching valves for automated clean up routines. The dual heater control and updated software provides the ability to warm the tray which has uses for (a) faster drying (b) enzyme digestion on the tray at 37° C. (c) better stability of sample as the heated tray makes up for the calories lost during evaporation.

It should be understood that various changes and modifications to the embodiments described herein would be apparent to those skilled in the art. Such changes and modifications can be made without departing from the spirit and scope of the presently disclosed subject matter. It is therefore intended that such changes and modifications be covered by the appended claims. The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

Effect of Tray Temperature on Matrix Deposition and Mass Spectrometry Imaging[1]

[1] As presented in HTX App Note #41.

To achieve high spatial resolution imagines, it is essential to evenly deposit matrix on tissue sections without letting the matrix crystals grow too large. While some matrices are known to generate fine crystals, 2,5-dihydroxybenzoic acid (DHB), which is one of the most commonly used matrices, is known to form large needle-shaped crystals. The sprayer used (HTX M5 sprayer, available from HTX Imaging) featuring a heated tray that can apply elevated temperature to the slide while spraying matrix. The effect of tray temperature on matrix deposition and the quality of high resolution MS imaging analysis was determined.

Flow rat brain embedded in 10% gelatin solution was fresh frozen and cryosectioned in sagittal sections at 12 microns on a cryomicrotome (Leica CM 3050 S, available from Leica Biosystems, Buffalo Grove, Ill., United States). Tissues were thaw-mounted onto indium-tin-oxide coated glass slides and kept frozen at −80° C. until analysis. Prior to matrix deposition, slides were kept in a desiccator at room temperature for 30 minutes. No pre-treatment or washing step was used.

DHB was applied to the slides at a concentration of 30 mg/mL (in 50:50 methanol:water) using the M5 sprayer. The slides were coated using the parameters set forth in Table 2. Matrix was applied using the sprayer as described in Table 1.

TABLE 1

Matrix Application Parameters

| Parameter | Condition |
|---|---|
| Flow Rate (mg/mL) | 0.1 |
| Spray Nozzle Velocity (mm/min) | 1000, 1500, or 2000 |
| Spray Nozzle Temp. (° C.) | 75 |
| Tray Temp.* (° C.) | 25, 35, 45, or 55 |
| Track Spacing (mm) | 3 |
| Number of Passes | 8, HH pattern |

*To minimize exposure time to elevated temperature, slide was kept off the tray until the target temperature was reached. The slide was then placed on the tray to balance temperature for 1 minute prior to spraying. After spraying, the slide was taken off the tray immediately and placed in a desiccator.

TABLE 2

Specific Settings for Each Condition

| Condition | 1 | 2 | 3 | 4 | 5 | 6 |
|---|---|---|---|---|---|---|
| Tray Temp. (° C.) | 55 | 45 | 35 | 25 | 25 | 25 |
| Nozzle Velocity (mm/min) | 1000 | 1000 | 1000 | 1000 | 1500 | 2000 |
| Resulting Matrix Density ($\mu g/mm^2$)* | 8 | 8 | 8 | 8 | 5.3 | 4 |

*Matrix density (W) was calculated by the equation Matrix Density = (NP × FR × C)/(V × TS), where NP: number of passes; C: concentration of matrix (mg/mL); FR: flow rate (mL/min); V: nozzle velocity (mm/min); TS: track spacing (mm).

The matrix-coated slides were examined under a light microscope (Eclipse Ni-U microscope, available from Nikon Instruments, Inc., Melville, N.Y., United States) at 4× and 10× for both on-tissue and off-tissue areas. FIGS. 9a-12f illustrate microscopic photographs of matrix-coated slides. As shown, FIGS. 9a-9f illustrate 4× magnified images of 6 samples of on-tissue areas. FIGS. 10a-10f illustrate 10× magnified images of 6 samples of on-tissue areas. FIGS. 11a-11f illustrate 4× magnified images of 6 samples of off-tissue areas. FIGS. 12a-12f illustrate 10× magnified images of 6 samples of off-tissue areas.

MS imaging experiments were performed on a MALDI-Orbitrap system, where a MALDI/ESI injector (available from Spectroglyph, LLC, Kennewick, Wash., United States) was coupled to an Orbitrap Velos mass spectrometer (available from Thermo Scientific, Waltham, Mass., United States) for high resolution MS analysis. The MALDI source was equipped with an Explorer One Nd:YLF (349 nm) laser firing at 2000, resolving power of 7500 (at m/z 400) with a maximum injection time of 50 ms (automatic gain control target at 1e6).

Rat cerebellum and brain stem areas were selected for imaging at a pixel size of 25 μm. Condition 5 & 6 were not imaged due to poor matrix coverage.

Slides sprayed with DHB at various conditions were examined under the microscope for comparison (FIGS. 9-12). It was determined that matrix density of 8 ug/mm$^2$, which corresponded to a nozzle velocity of 1000 mm/min (condition 1-4), gave good coverage on both on-tissue and off-tissue areas. Matrix densities of 5.3 (condition 5) and 4 (condition 6) were not able to provide good coverages. Due to the long imaging time at high spatial resolution, condition 5 and 6 were not selected for mass spectrometry imaging analysis. Comparing the slides with same matrix density, slides sprayed with higher temperatures tend to generate finer DHB crystals compared to the ones sprayed with lower temperature. For example, 10× on-tissue figures (FIG. 9b) revealed fine crystal structures for conditions 1 and 2 (55° C. and 45° C.), but visible needle shape structures for conditions 3 and 4 (35° C. and 25° C.). The same trend was observed for off-tissue areas. Therefore, it was determined that increasing the tray temperature during matrix spraying helped reduce matrix crystal size, which is essential for high spatial resolution MS images.

Example 2

Method of Fast Spray Deposition[2]

[2] As presented in scientific poster titled "M5 TM-Sprayer Applications for High Resolution Accurate Mass Imaging by MALDI FT-ICR", Alyson Black et al., MUSC Taking advantages of the higher nozzle velocity available on the HTX M5 Sprayer, a standard protocol for spray deposition of DAN matrix was optimized for time saving and resulted in a sample preparation of only 4.24 minutes, compared to 13.2 minutes for the standard protocol. In this experiment, the standard protocol comprised spraying 1-5-diaminoapthalene matrix (DAN, 5 mg/ml in 90% Acetonitrile) onto microscope glass slides. Other parameters were 10 passes at 77° C., 40 mm distance from spray head to medium, 3 mm offsets, 6 psi pressure, 1300 mm/min velocity (the maximum velocity on previous models), and 0.100 ml/min fluid flow rate. It was then proposed to compare the analysis and resulting image quality when doubling or tripling the spray velocity and the fluid flow rate. In theory, this would maintain the ratio of flow rate to velocity, aka linear flow rate, constant thus ensuring a similar spray wetness level.

Figure 24C:
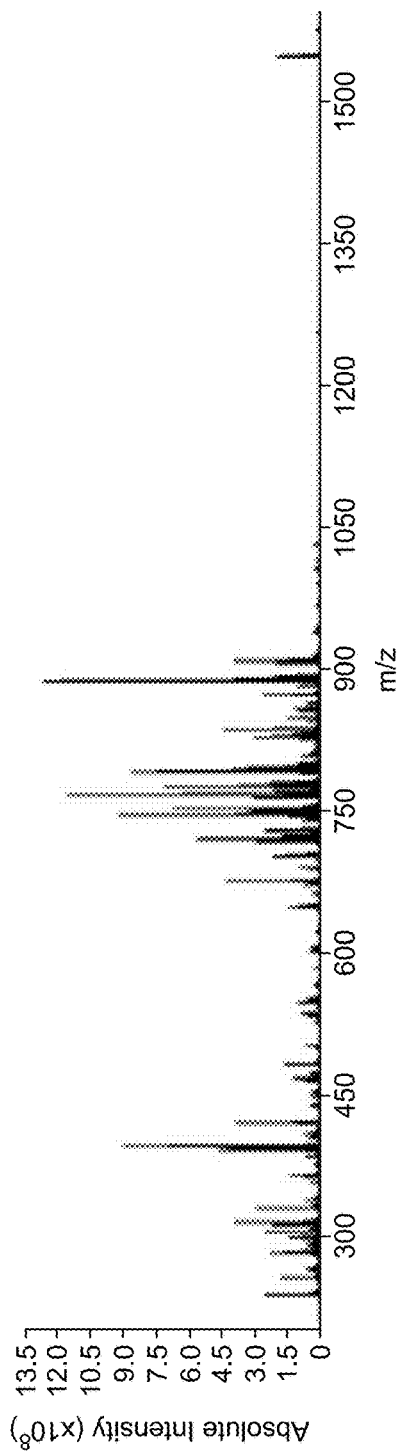
FIG. 24c is a graph of absolute intensity versus m/z illustrating the comparison of overall spectra at 3900 mm/min.

FIG. 21a-21e are images in negative mode of rat brain serial sections prepared on the M5 sprayer at velocities of 1300 mm/min (1× velocity, 13:20 mins per slide), with m/z of 744.5654, 747.4949, 766.5468, 885.5484, and 906.6431, respectively. FIGS. 22a-22e are images in negative mode of rat brain serial sections prepared on the M5 sprayer at velocities of 2600 mm/min (2× velocity, 6:40 mins per slide), with m/z of 744.5654, 747.4949, 766.5468, 885.5484, and 906.6431, respectively. FIGS. 23a-23e are images in negative mode of rat brain serial sections prepared on the M5 sprayer at velocities of 3900 mm/min (3× velocity, 4:24 mins per slide), with m/z of 744.5654, 747.4949, 766.5468, 885.5484, and 906.6431, respectively. FIGS. 24a-24c are graphs of the absolute intensity (×10$^6$) versus m/z from the data of FIGS. 21a-21e, 22a-22e, and 23a-23e, respectively. FIGS. 24a-24c illustrate a comparison of overall spectra at 1300, 2600, and 3900 mm/min. The spectra were normalized by Total Ion Current (TIC) normalization.

The results shown in FIGS. 21-24 show that the data quality was maintained through all three sets of images, but the protocols using a velocity of 3,900 mm/min and flow rate of 0.300 ml/min was three times faster (4.24 minutes compared to 13.2 minutes). These improvements are especially important for medical and diagnostic applications where sample preparation can be the limiting time factor to obtaining a test result.

Example 3[3]

[3] From Vanderbilt University.

Super Dry Spray Conditions for Drying of THAP and Other Difficult-to-Dry Matrices 2,4,6 Trihydroxyacetophenone (THAP) offers great potential for MALDI analysis and imaging of lipids, acidic glycans, and glycol-peptides in negative ion mode. However, spray deposition of THAP is challenging due to its tendency to form hydrates. When deposited by spray under normal conditions, the hydrated solution results in a liquid film layer that dries very slowly and forms a non-uniform coating. In the proposed protocol, a 2-step process was devised to deposit THAP successfully and to create high resolution MS images.

Taking advantage of the high velocity of the XY stage of the HTX M5 Sprayer, the first four layers were deposited in super dry mode (LFR less than 0.0000083 ml/mm) to create a seeding layer. The next four layers (better optimized for extraction) were then deposited on top, resulting in a very good balance of analytes extraction, high signal intensity, and limited spatial delocalization. The protocol did not require rehydration to produce a high intensity spectrum. Table 3 lists the protocol:

TABLE 3

| | Protocol for Layers 1-4, 5-8 | |
|---|---|---|
| | Matrix | 2,4,6-THAP at 1 mg/ml in 100% acetone |
| First 4 layers | Flow Rate (ml/min) | 0.050 |
| | Velocity (mm/min) | 2,000 |
| | Temperature (° C.) | 30 |

TABLE 3-continued

| | Protocol for Layers 1-4, 5-8 | |
|---|---|---|
| | Track Spacing (mm) | 1.5 |
| | Matrix | 2,4,6-THAP at 11.1 mg/ml in 66% chloroform, 34% methanol |
| Second 4 layers | Flow Rate (ml/min) | 0.100 |
| | Velocity (mm/min) | 3,600 |
| | Temperature (° C.) | 30 |
| | Track Spacing (mm) | 1.5 |

Figure 13A:
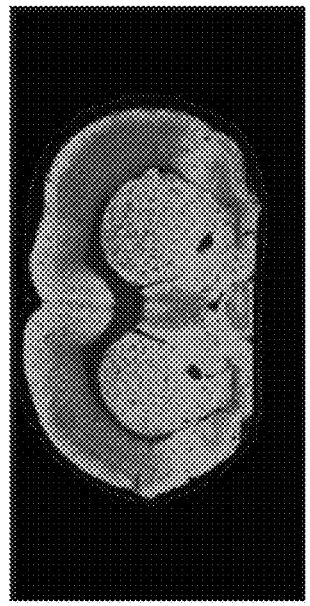
FIGS. 13a-13d are MS images of lipid species detected on 4 samples of rat brain.
Figure 13B:
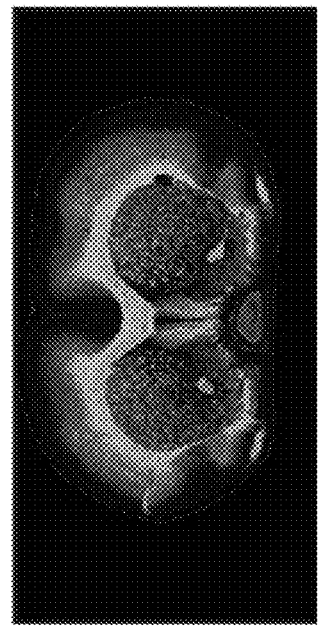
Figure 13C:
Figure 13D:
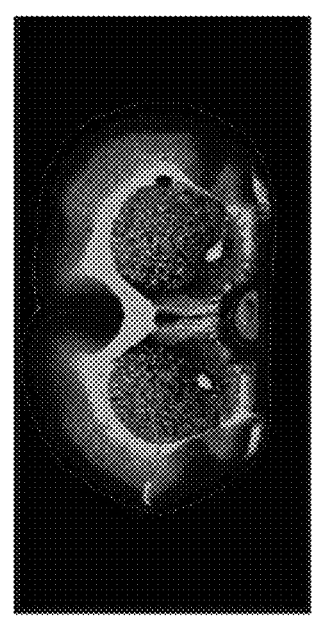

A Bruker Rapiflex Tissue Typer was used produce 15 micron images showing high resolution of lipids at m/z 806.3 (FIG. 13a), 885.3 (FIG. 13b), 888.4 (FIG. 13c), and 906 Daltons (FIG. 13d).

Figure 13E:
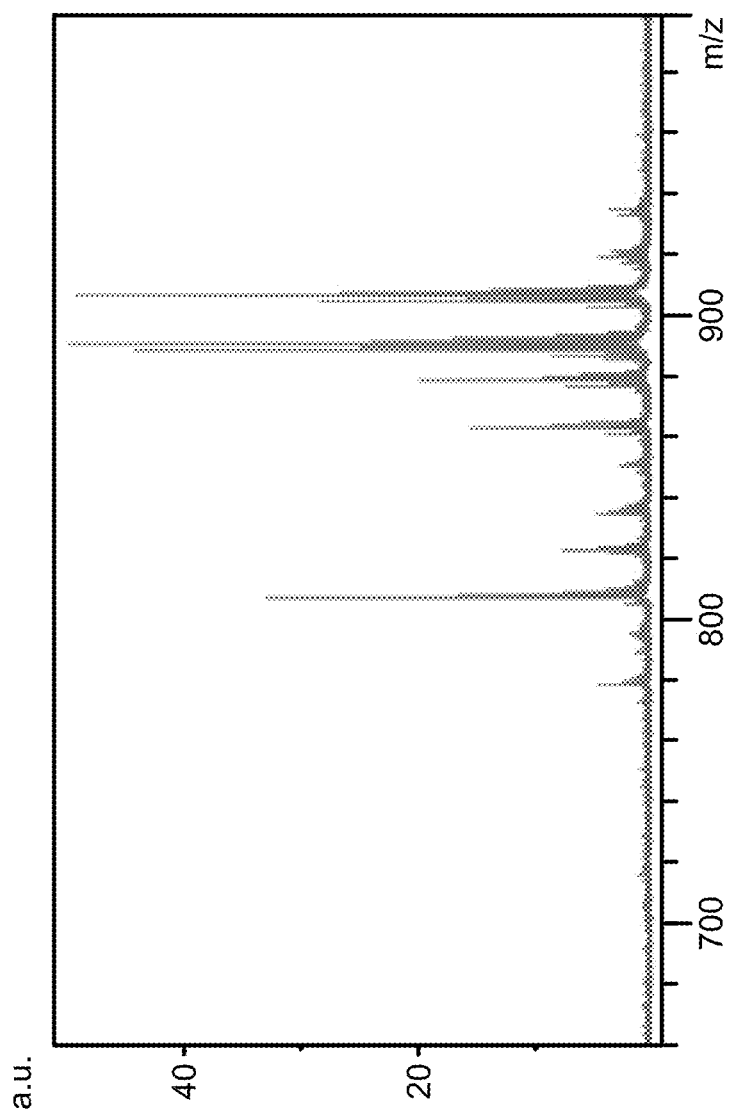
FIG. 13e is a spectrum corresponding to FIGS. 13a-13d, illustrating the high intensity MS signal.

FIG. 13e illustrates a spectrum corresponding to FIGS. 13a-13d, illustrating the high intensity MS signal.

Example 4

High Resolution MS Imaging Analysis[4]

[4] From Maastricht University.

Rat cerebellum and brain stem areas were selected for high resolution MS imaging analysis at 25 um (conditions 1-4). A common lipid list of 350 species was used to map distribution, and selected ion images are shown in FIGS. 14a-17d. FIGS. 14a-14d illustrate MS images of lipid species detected on 4 samples of rat brain with m/z value of 756.55138, PC (16:0/16:0)+Na. FIGS. 15a-15d illustrate MS images of lipid species detected on 4 samples of rat brain with m/z value of 760.58508, PC (16:0/18:1)+H. FIGS. 16a-16d illustrate MS images of lipid species detected on 4 samples rat brain with m/z value of 767.56977, phSM (16:0/22:5)+H. FIGS. 17a-17d illustrate MS images of lipid species detected on 4 samples of rat brain with m/z value of 864.64768.

Example 5—from Maastricht University[4]

[4] From Maastricht University.

Use of Environmentally-Friendly Solvent Solutions

Using a well-validated matrix spray deposition protocol with Norhamane matrix dissolved at 7 m/ml in 2:1 Chloroform:Methanol (Protocol NOR-01) that provides high resolution images of lipids, reducing the ratio of chloroform to methanol to 1:1 and 2:1 was investigated. The signal intensity and image spatial resolution were also compared.

Figure 18A:
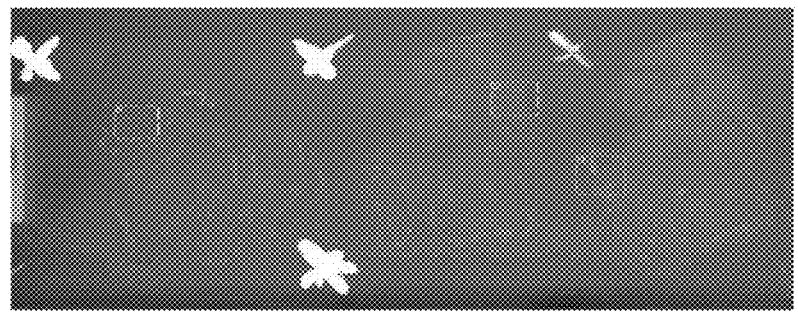
FIG. 18a is an optical image of the prepared sample with matrix dissolved in 2:1 chloroform:methanol applied by spray, and identifying zone 01.
Figure 18B:
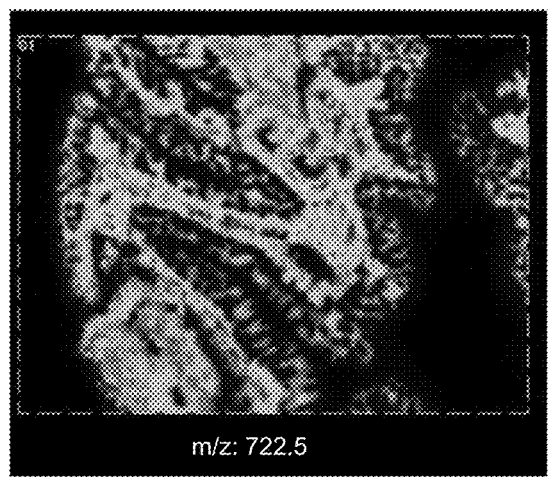
FIGS. 18b-18d are mass spectrometry analysis of zone 01 from FIG. 18a, showing evidence of lipids m/z 722.5, 863.5 and 885.5 at 20 micron resolution.
Figure 18C:
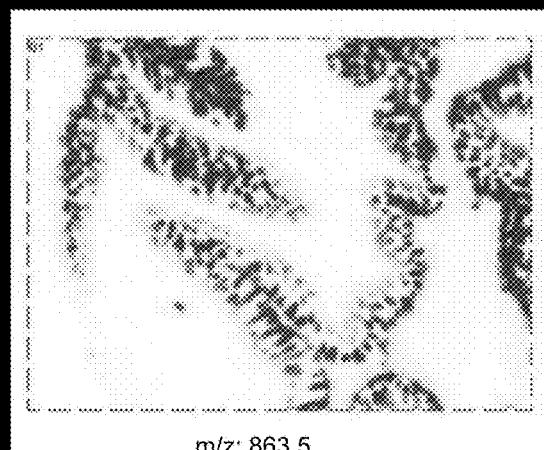
Figure 18D:
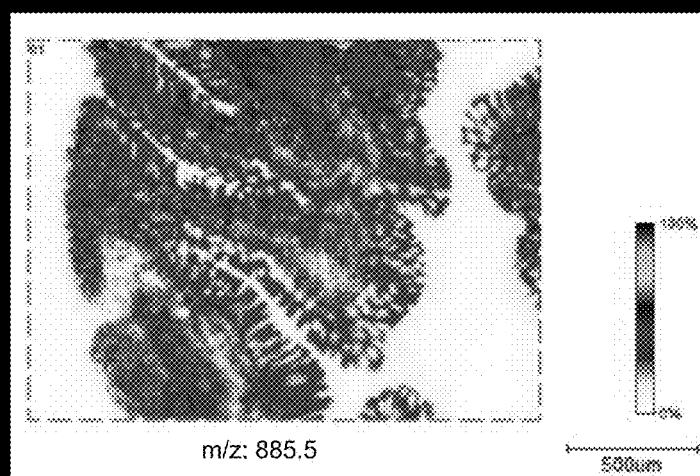

As shown in FIGS. 18a-18d, image characteristics are maintained at a 1:1 chloroform:methanol ratio. Particularly, FIG. 18a illustrates matrix images from high spatial resolution imaging using a Rapiflex® MALDI Tissuetyper® with a pixel size of 20 μm. FIGS. 18b-18d are mass spectrometry analysis of zone 01 from FIG. 18a, showing evidence of lipids m/z 722.5, 863.5 and 885.5 at 20 micron resolution.

Figure 19A:
FIG. 19a is an optical image of the prepared sample with matrix dissolved in 1:1 chloroform:methanol applied by spray, and identifying zone 01, 02 and 03.
Figure 19B:
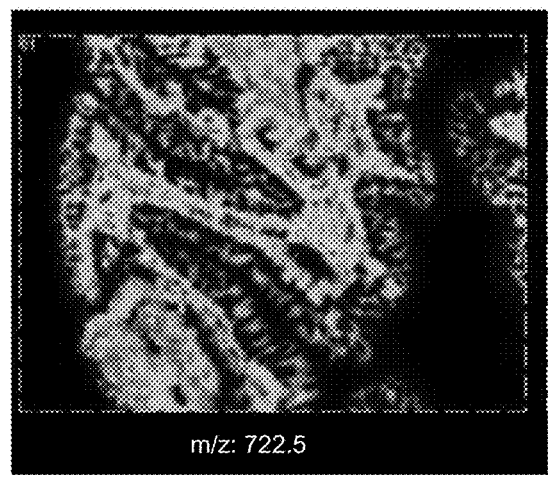
FIGS. 19b-19d are mass spectrometry analysis of zone 01, 02 and 03 from FIG. 19a, showing evidence of lipids m/z 722.5 at 20 micron resolution.
Figure 19C:
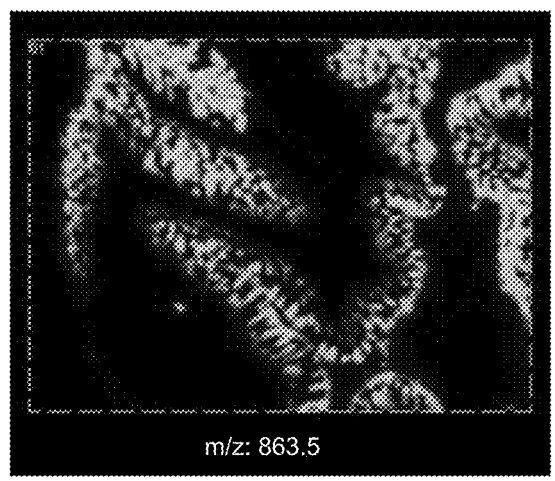
Figure 19D:
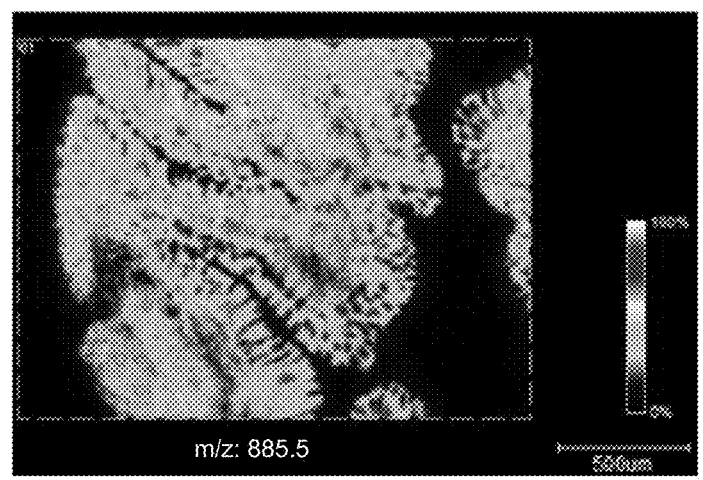
Figure 20A:
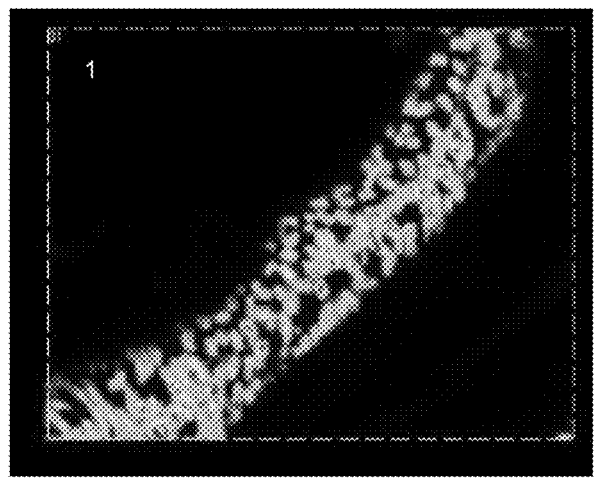
FIGS. 20a-20f are mass spectrometry image analysis of zone 01, 02 and 03 from FIG. 19a, showing evidence of lipids m/z 863.5 at 20 micron resolution.
Figure 20B:
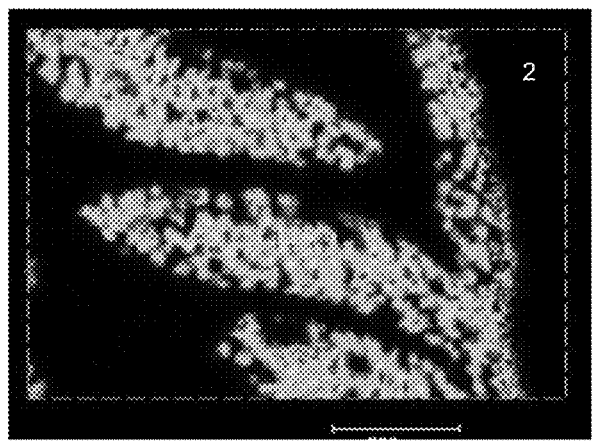
Figure 20C:
Figure 20D:
Figure 20E:
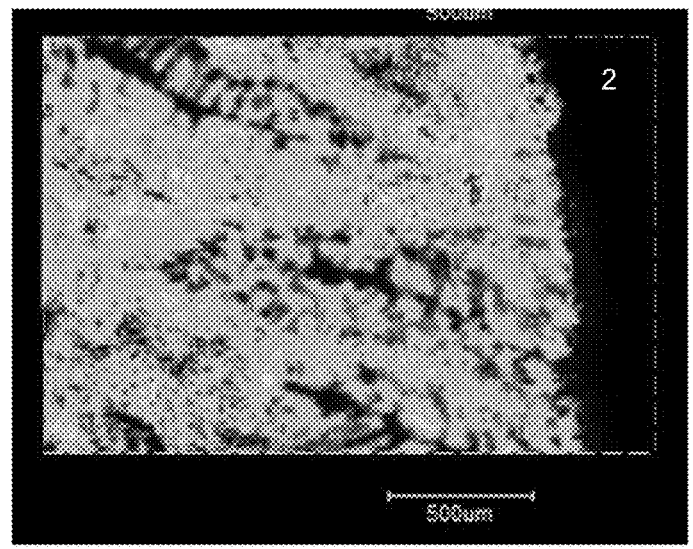
Figure 20F:
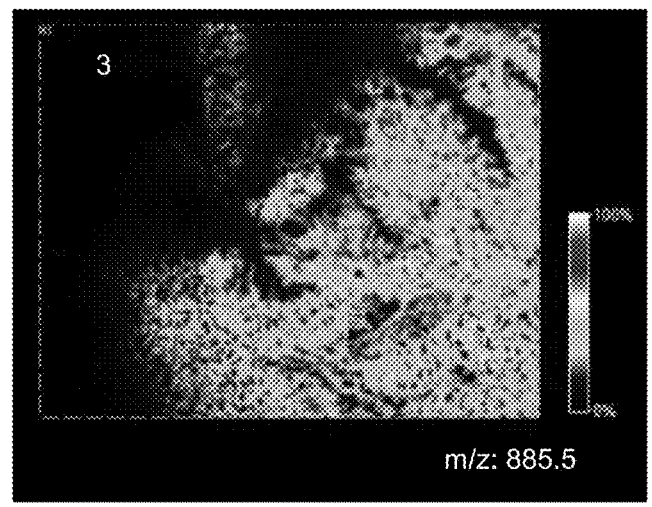
Figures 21A, 21B, 21C, 21D, 21E:
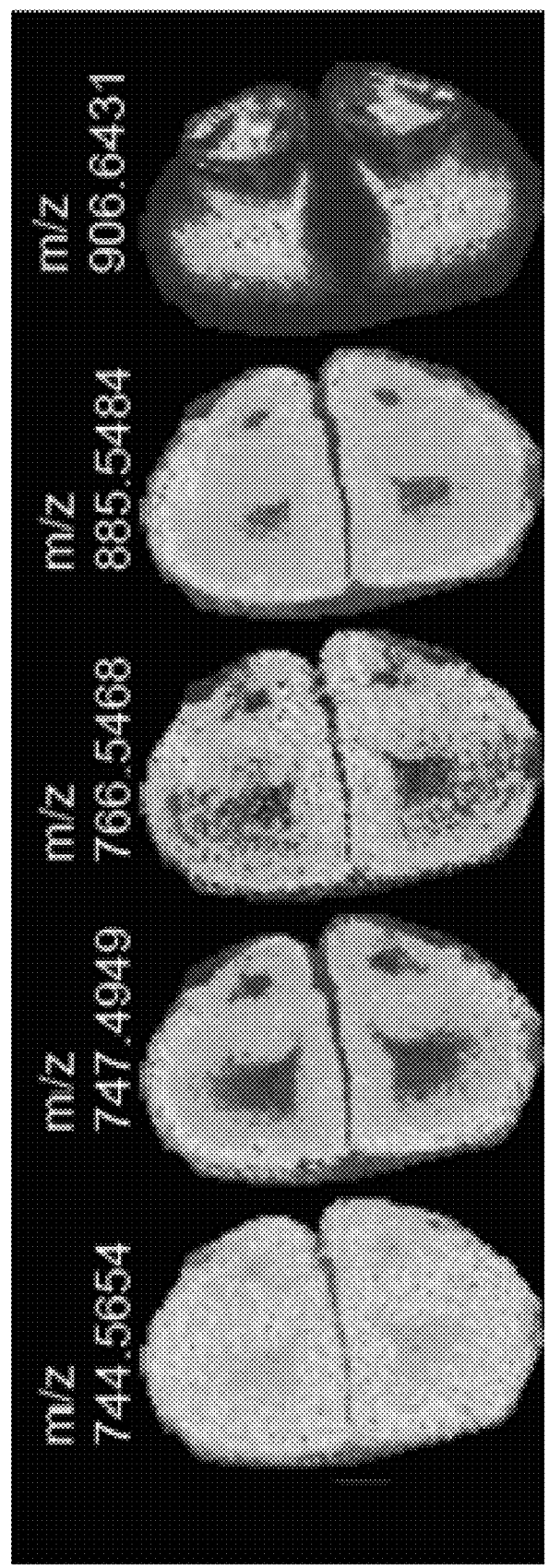
FIGS. 21a-21e are images in negative mode of rat brain serial sections prepared on the M5 sprayer at velocities of 1300 mm/min.
Figures 22A, 22B, 22C, 22D, 22E:
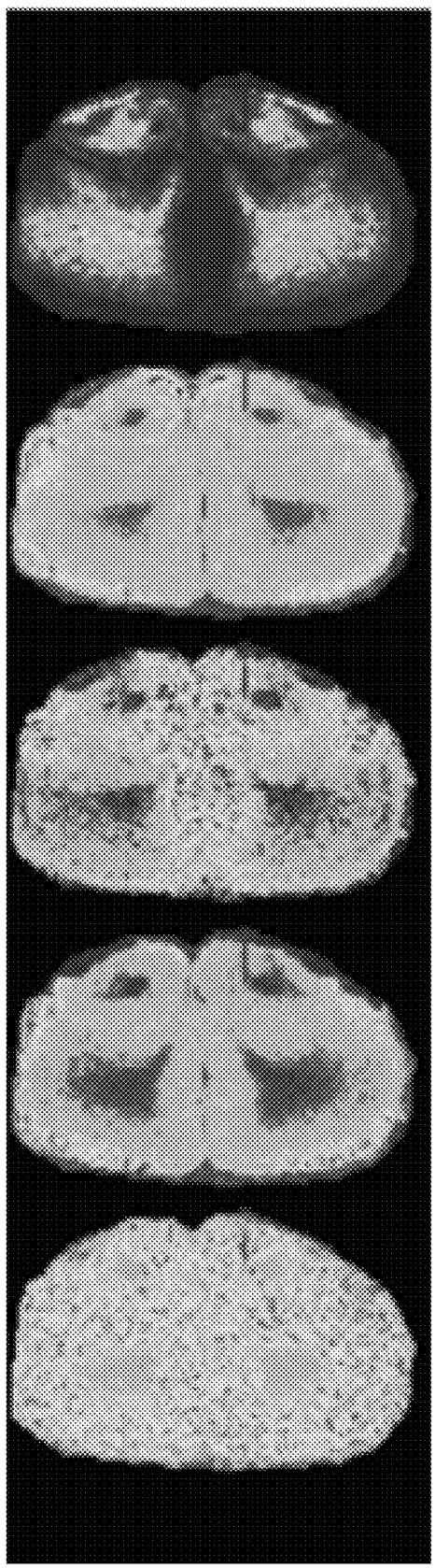
FIGS. 22a-22e are images in negative mode of rat brain serial sections prepared on the M5 sprayer at velocities of 2600 mm/min.
Figures 23A, 23B, 23C, 23D, 23E:
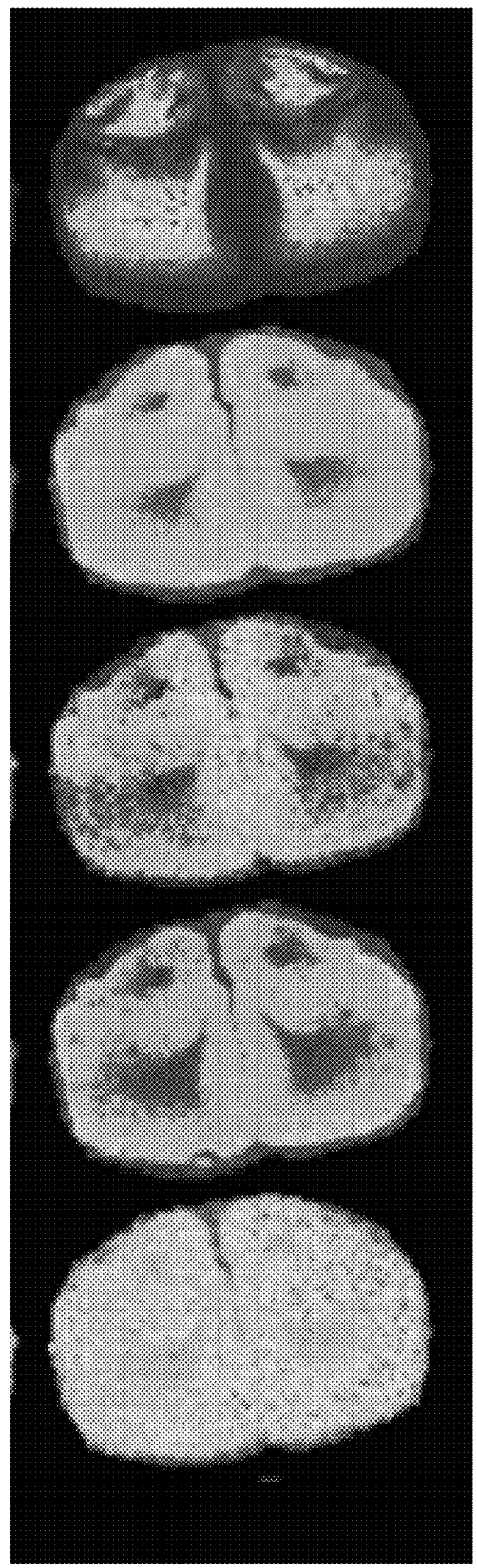
FIGS. 23a-23e are images in negative mode of rat brain serial sections prepared on the M5 sprayer at velocities of 3900 mm/min.

The experiment using the 2:1 ratio of chloroform to methanol showed poor spatial resolution which can be corrected by increasing temperature. For example, FIG. 19a shows matrix images from high spatial resolution imaging using a Rapiflex® MALDI Tissuetyper® with a pixel size of 20 μm. FIGS. 19b-19d are mass spectrometry analysis of zone 01, 02 and 03 from FIG. 19a, showing evidence of lipids m/z 722.5 at 20 micron resolution.

FIGS. 20a-20f are mass spectrometry analysis of zone 01, 02 and 03 from FIG. 19a, showing evidence of lipids m/z 863.5 at 20 micron resolution.

CONCLUSIONS

The results herein indicate that generating fine matrix crystal is essential for high resolution MS imaging. Applying DHB matrix at elevated tray temperature can be used to create fine matrix crystals, resulting in sharper and more intense MS image signals.

What is claimed is:

1. A system for depositing a chemical layer of one or more components onto a medium, comprising:
   a spray assembly for depositing the chemical layer, including:
      a capillary for receiving and ejecting a fluid comprising the one or more components, wherein the capillary comprises an exit through which the fluid is sprayed;
      a nozzle body configured to channel a gas towards the exit of the capillary and configured to atomize a fluid into a directional spray that delivers droplets with a diameter of 0.1-1.0 microns onto a medium; and
      a heat exchanger housed in the nozzle body for heating the capillary and the gas;
   an enclosure for housing the medium and the spray assembly, the enclosure comprising:
      a translatable drawer for supporting the medium and translating the medium into an interior of the enclosure; and
      a fan venting system for exhausting solvent fumes,
   wherein the drawer comprises a medium support tray that includes inserts, position measurements, pre-defined positions for laboratory equipment, or combinations thereof, and wherein the drawer provides no viewing bias.

2. The system of claim 1, wherein the spray assembly is translatably coupled with a first arm to allow perpendicular movement of the spray assembly about the first arm and translatably coupled with a second arm to allow perpendicular movement of the spray assembly about the second arm for maneuvering the spray assembly with respect to the medium at a nozzle velocity of about 1,200 to 5,600 mm/min.

3. The system of claim 2, wherein the spray assembly includes a pump in communication with the nozzle body, wherein the pump is configured to adjust the fluid flow rate in relation to the nozzle velocity to provide a linear flow rate of less than about 0.00001 ml/mm.

4. The system of claim 2, wherein the spray assembly is configured for spray deposition at a velocity of about 18,000 mm/min or less, wherein the spray humidity measurement is selected from calculated linear flow rate, sensor-controlled evaporation rate, or combinations thereof.

5. The system of claim 2, wherein the spray assembly is configured to spray in a defined spray pattern, selected from Swiss Cross, automatic square, non-overlapping, diagonal, and combinations thereof.

6. The system of claim 1, where the translatable drawer comprises a medium heater to allow control of the medium from temperatures of about −20° C. to 120° C.

7. The system of claim 6, wherein the system is configured to:
decrease the matrix crystal size below 10 micron;
enable the use of difficult-to-dry matrices;
allow the use of environmentally friendly solvent mixtures comprising a greater weight percent of water, methanol, or both compared to a relatively smaller weight percent of highly volatile solvents; or
combinations thereof.

8. The system of claim 6, further including a humidity chamber to perform one or more temperature and humidity-controlled reactions, selected from enzymatic digestion, derivatization, rehydration, or combinations thereof.

9. The system of claim 1, further comprising an air conditioner or a fan that is configured to regulate humidity, pressure, temperature, or combinations thereof within an interior of the compartment.

10. The system of claim 1, wherein the enclosure further comprises a front viewing panel positioned above a front panel of the translatable drawer, and a gutter positioned within the enclosure on one of the two opposing side panels for collecting fluid so that waste materials are contained when the translatable drawer is open.

11. The system of claim 1, wherein the drawer further includes:
a motorized open and close feature;
a gripping feature to allow manual drawer translation or integration with a robotic device; or
combinations thereof.

12. The system of claim 1, wherein the spray heater includes a fluid spray heater and a gas spray heater, each being independently operable and capable of being set at different temperatures.

13. The system of claim 1, further including an external heater for heating the fluid, gas, or both before being received by the spray assembly.

14. The system of claim 1, further including at least one additional capillary for receiving and ejecting a fluid comprising one or more secondary components.

15. The system of claim 1, further including at least one additional nozzle for receiving and ejecting an additional gas towards the medium, the fluid, or both when the fluid is ejected from the capillary.

16. The system of claim 1, further including one or more switching valves for switching from a first fluid or gas to a second fluid or gas, wherein the switching valve optionally comprises a combination of a selector valve and multiple loop valves capable of maintaining a constant flow rate while changing fluid or gas type.

17. The system of claim 16, further including a software-controlled solvent pump, a selector valve, and one or more switching valves to allow automated start-up, medium spraying, cleaning sequence, and shut-down.

18. The system of claim 1, further including a fluid line and capillary capable of withstanding solvent pressure greater than 14.7 psi, and a pump configured for bringing a fluid within the fluid line or capillary to its boiling point temperature at ambient pressure.

19. The system of claim 1, wherein the nozzle body and heat exchanger are configured with a length, width, or both of less than about 3.5 inches.

20. A system for depositing a chemical layer of one or more components onto a medium, comprising:
a spray assembly for depositing the chemical layer, including:
a capillary for receiving and ejecting a fluid comprising the one or more components, wherein the capillary comprises an exit through which the fluid is sprayed;
a nozzle body configured to channel a gas towards the exit of the capillary and configured to atomize a fluid into a directional spray that delivers droplets with a diameter of 0.1-1.0 microns onto a medium; and
a heat exchanger housed in the nozzle body for heating the capillary and the gas;
an enclosure for housing the medium and the spray assembly, the enclosure comprising:
a translatable drawer for supporting the medium and translating the medium into an interior of the enclosure; and
a fan venting system for exhausting solvent fumes,
a humidity chamber to perform one or more temperature and humidity-controlled reactions, selected from enzymatic digestion, derivatization, rehydration, or combinations thereof;
wherein the translatable drawer comprises a medium heater to allow control of the medium from temperatures of about −20° C. to 120° C.

21. A system for depositing a chemical layer of one or more components onto a medium, comprising:
a spray assembly for depositing the chemical layer, including:
a capillary for receiving and ejecting a fluid comprising the one or more components, wherein the capillary comprises an exit through which the fluid is sprayed;
a nozzle body configured to channel a gas towards the exit of the capillary and configured to atomize a fluid into a directional spray that delivers droplets with a diameter of 0.1-1.0 microns onto a medium; and
a heat exchanger housed in the nozzle body for heating the capillary and the gas;
an enclosure for housing the medium and the spray assembly, the enclosure comprising:
a translatable drawer for supporting the medium and translating the medium into an interior of the enclosure; and
a fan venting system for exhausting solvent fumes,
at least one additional nozzle for receiving and ejecting an additional gas towards the medium, the fluid, or both when the fluid is ejected from the capillary.

* * * * *